US008744558B2

(12) United States Patent
Mower

(10) Patent No.: US 8,744,558 B2
(45) Date of Patent: Jun. 3, 2014

(54) METHOD AND APPARATUS FOR PROVIDING IPSELATERAL THERAPY

(75) Inventor: Morton M. Mower, Baltimore, MD (US)

(73) Assignee: Mirowski Family Ventures, L.L.C., Washington, DC (US)

(*) Notice: Subject to any disclaimer, the term of this patent is extended or adjusted under 35 U.S.C. 154(b) by 1099 days.

(21) Appl. No.: 11/692,114

(22) Filed: Mar. 27, 2007

(65) Prior Publication Data
US 2007/0191893 A1 Aug. 16, 2007

Related U.S. Application Data

(63) Continuation of application No. 10/654,959, filed on Sep. 5, 2003, now abandoned.

(51) Int. Cl.
A61N 1/362 (2006.01)

(52) U.S. Cl.
USPC .............................. 600/510; 607/9

(58) Field of Classification Search
USPC .................. 607/9, 14, 15; 600/510
See application file for complete search history.

(56) References Cited

U.S. PATENT DOCUMENTS

| 3,345,990 | A | 10/1967 | Berkovits |
| 3,431,912 | A | 3/1969 | Keller, Jr. |
| 3,433,228 | A | 3/1969 | Keller, Jr. |
| 3,595,242 | A | 7/1971 | Berkovits |
| 3,648,707 | A | 3/1972 | Greatbach |
| 3,747,604 | A | 7/1973 | Berkovits |
| 3,814,106 | A | 6/1974 | Berkovits |
| 3,903,897 | A | 9/1975 | Woollons et al. |
| 3,937,226 | A | 2/1976 | Funke |
| 4,052,991 | A | 10/1977 | Zacouto |
| 4,057,067 | A | 11/1977 | Lajos |
| 4,088,140 | A | 5/1978 | Rockland et al. |
| 4,303,075 | A | 12/1981 | Heilman et al. |
| 4,312,355 | A | 1/1982 | Funke |

(Continued)

FOREIGN PATENT DOCUMENTS

| EP | 0017447 A1 | 10/1980 |
| EP | 0039269 A1 | 11/1981 |

(Continued)

OTHER PUBLICATIONS

Morton M. Mower, U.S. Appl. No. 10/214,474, entitled "Method and Apparatus for Treating Hemodynamic Disfunction," filed Aug. 8, 2002 (Continuation Reissue Application of U.S. Patent No. 4,928,688).

(Continued)

Primary Examiner — Rex R Holmes
(74) Attorney, Agent, or Firm — Oblon, Spivak, McClelland, Maier & Neustadt, L.L.P.

(57) ABSTRACT

Methods, apparatus, and systems are provided to control contraction of the heart. At least one sensing element receives signals indicating electrical activity of sinus rhythm of the heart. The electrical activity is monitored and analyzed to detect an event. In addition, the electrical activity is monitored to detect, for example, premature stimulation and contraction of a portion of the heart, such as the left ventricle. Contraction in the pre-excited portion of the heart is then suppressed using electrical pulses. The heart may then be allowed to contract naturally, or a stimulating pulse may be applied to assist the heart in contracting.

10 Claims, 5 Drawing Sheets

(56) References Cited

U.S. PATENT DOCUMENTS

| | | |
|---|---|---|
| 4,332,259 A | 6/1982 | McCorkle, Jr. |
| 4,335,727 A | 6/1982 | McPherson |
| 4,354,497 A | 10/1982 | Kahn |
| 4,378,020 A | 3/1983 | Nappholz et al. |
| 4,386,610 A | 6/1983 | Leckrone |
| 4,401,119 A | 8/1983 | Herpers |
| 4,418,695 A | 12/1983 | Buffet |
| 4,429,697 A | 2/1984 | Nappholz et al. |
| 4,452,248 A | 6/1984 | Keller, Jr. |
| 4,458,677 A | 7/1984 | McCorkle, Jr. |
| 4,541,417 A | 9/1985 | Krikorian |
| 4,548,203 A | 10/1985 | Tacker, Jr. et al. |
| 4,554,922 A | 11/1985 | Prystowsky et al. |
| 4,559,946 A | 12/1985 | Mower |
| 4,561,442 A | 12/1985 | Vollmann et al. |
| 4,624,260 A | 11/1986 | Baker, Jr. et al. |
| 4,628,934 A | 12/1986 | Pohndorf et al. |
| 4,641,656 A | 2/1987 | Smits |
| 4,685,446 A | 8/1987 | Choy |
| 4,705,043 A | 11/1987 | Imran |
| 4,712,555 A | 12/1987 | Thornander et al. |
| 4,727,877 A | 3/1988 | Kallok |
| 4,774,950 A | 10/1988 | Cohen |
| 4,790,317 A | 12/1988 | Davies |
| 4,799,486 A | 1/1989 | DuFault |
| 4,817,608 A | 4/1989 | Shapland et al. |
| 4,827,932 A | 5/1989 | Ideker et al. |
| 4,827,934 A | 5/1989 | Ekwall |
| 4,830,006 A | 5/1989 | Haluska et al. |
| 4,925,443 A | 5/1990 | Heilman et al. |
| 4,928,688 A | 5/1990 | Mower |
| 4,932,407 A | 6/1990 | Williams |
| 4,958,632 A | 9/1990 | Duggan |
| 4,967,749 A | 11/1990 | Cohen |
| 4,974,588 A | 12/1990 | Smits |
| 4,998,975 A | 3/1991 | Cohen et al. |
| 5,014,696 A | 5/1991 | Mehra |
| 5,024,222 A | 6/1991 | Thacker |
| 5,083,563 A | 1/1992 | Collins |
| 5,099,838 A | 3/1992 | Bardy |
| 5,111,811 A | 5/1992 | Smits |
| 5,129,394 A | 7/1992 | Mehra |
| 5,158,097 A | 10/1992 | Christlieb |
| 5,165,403 A | 11/1992 | Mehra |
| 5,174,289 A | 12/1992 | Cohen |
| 5,213,098 A | 5/1993 | Bennett et al. |
| 5,251,621 A | 10/1993 | Collins |
| 5,318,593 A | 6/1994 | Duggan |
| 5,334,222 A | 8/1994 | Salo et al. |
| 5,385,579 A | 1/1995 | Helland |
| 5,403,356 A | 4/1995 | Hill et al. |
| 5,545,204 A | 8/1996 | Cammilli et al. |
| 5,551,427 A | 9/1996 | Altman |
| 5,584,868 A | 12/1996 | Salo et al. |
| 5,626,620 A | 5/1997 | Kieval et al. |
| 5,755,766 A | 5/1998 | Chastain et al. |
| 5,800,464 A * | 9/1998 | Kieval ............... 607/9 |
| 5,800,465 A | 9/1998 | Thompson et al. |
| 5,814,079 A * | 9/1998 | Kieval ............... 607/4 |
| 5,871,506 A | 2/1999 | Mower |
| 5,899,930 A | 5/1999 | Flynn et al. |
| 5,902,324 A | 5/1999 | Thompson et al. |
| 5,919,209 A | 7/1999 | Schouten |
| 5,935,160 A | 8/1999 | Auricchio et al. |
| 6,067,470 A | 5/2000 | Mower |
| 6,136,019 A | 10/2000 | Mower |
| 6,141,586 A | 10/2000 | Mower |
| 6,141,587 A | 10/2000 | Mower |
| 6,178,351 B1 | 1/2001 | Mower |
| 6,185,459 B1 | 2/2001 | Mehra et al. |
| 6,295,470 B1 | 9/2001 | Mower |
| 6,298,268 B1 | 10/2001 | Ben-Haim et al. |
| 6,317,631 B1 | 11/2001 | Ben-Haim et al. |
| 6,330,476 B1 | 12/2001 | Ben-Haim et al. |
| 6,332,096 B1 | 12/2001 | Mower |
| 6,337,995 B1 | 1/2002 | Mower |
| 6,341,235 B1 | 1/2002 | Mower |
| 6,343,232 B1 | 1/2002 | Mower |
| 6,411,845 B1 | 6/2002 | Mower |
| 6,463,324 B1 | 10/2002 | Ben-Haim et al. |
| RE38,119 E | 5/2003 | Mower |
| 6,937,895 B1 | 8/2005 | Lu |

FOREIGN PATENT DOCUMENTS

| | | |
|---|---|---|
| EP | 0 494 487 A2 | 1/1996 |
| EP | 0 726 082 A2 | 8/1996 |
| EP | 1 249 254 A2 | 10/2002 |
| GB | 2119255 A | 7/1975 |
| GB | 1401247 | 11/1983 |
| WO | WO 82/03783 | 11/1982 |
| WO | WO 86/05698 | 10/1986 |

OTHER PUBLICATIONS

Picture of Biventricular Pacer manufactured by American Optical Co., American Optical Corp., Research Division, Biventricular Pacer Device, 1975.

Aranda et al., "A New Pacemaker for Simultaneous Biventricular Stimulation of the Human Heart," Clin. Res., vol. XXIV, No. 3, p. 206A (1976).

Badeer, "Relation of ECG to Mechanical Events," *Cardiovascular Physiology*, 1984, 6:57-58.

Bailon et al., "Some Data for an Unanswered Question: Choosing the Ventricular Electrode Place," Pacing and Clinical Electrophysiology, vol. 8, No. 3, Part II, p. A-11 (1985).

Bakker et al., "Beneficial Effects of Biventricular Pacing in Congestive Heart Failure," PACE, Apr. 1994, 17 (4):820.

Bakker et al., "Biventricular Pacing in Congestive Heart Failure," *Clinical Research*, vol. 42, No. 2., Apr. 1994, p. 327A.

Bakker et al., "Biventricular Pacing Improves Functional Capacity in Patients with End-Stage Congestive Heart Failure," PACE, NASPE Abstracts 1995 (18):825.

Barold et al., "First Reports of Electrical Multisite Ventricular Activation in Humans," PACE, Dec. 2000, (23):2117-2119.

Bashir et al., "Combined Use of Transesophageal ECHO and Fluoroscopy for the Placement of Left Ventricular Pacing Leads Via the Coronary Sinus," PACE, Oct. 2003, (26):1951-1954.

Befeler et al., "Programmed Simultaneous Biventricular Stimulation in Man, with Special Reference to its Use in the Evaluation of Intraventricular Reentry," Eur. J. of Cardiology, vol. 9, No. 5, pp. 369-378 (1979).

Diotallevi et al., "Rescuing Failed Biventricular Implants Using Right Ventricular Bifocal Pacing to Assure Cardiac Resynchronization Benefits to Heart Failure Patients," Heart Rhythm, vol. 3, No. 5, May Supplement 2006, Abstract No. AB48-2.

Leclercq et al., "Triple Site Ventricular Pacing for Optimizing Ventricular Resynchronization: Design of the Trip-HF Study; Technical Feasibility," Heart Rhythm, vol. 3, No. 5, May Supplement 2006, Abstract No. AB48-3.

Niazi et al., "Dual-Site Left Ventricular Stimulation Provides Better Resynchronization Response than Conventional Biventricular Stimulation," Heart Rhythm, vol. 3, No. 5, May Supplement 2006, Abstract No. AB42-6.

Yoshida et al., "Tripolar-Ventricular Pacing Improves Both Systolic and Diastolic Left Ventricular Function in Patients with End-Stage Heart Failure," Heart Rhythm, vol. 3, No. 5, May Supplement 2006, Abstract No. P6-96.

Abraham, WT, et al., "Cardiac Resynchronization in Chronic Heart Failure," *N. Engl. J. Med.*, vol. 346, No. 24, 2002, pp. 1845-1853.

Anagnostopoulos, CE, et al., "Transvenous Coronary Sinus Pacemaker: A New Primary Approach to Heart Block in Patients with Tricuspid Prostheses," *The Annals of Thoracic Surgery*, vol. 9, No. 3, Mar. 1970, pp. 248-252.

Aurrichio A, et al, "Effect of Pacing Chamber and Atrioventricular Delay on Acute Systolic Function of Paced Patients With Congestive Heart Failure," *Circulation*, vol. 99, No. 23, Jun. 1999, pp. 2993-3001.

(56) References Cited

OTHER PUBLICATIONS

Aurrichio A, et al., "Long-Term Clinical Effect of Hemodynamically Optimized Cardiac Resynchronization Therapy in Patients With Heart Failure and Ventricular Conduction Delay," *J. Am. Coll. Cardiol.*, vol. 39, No. 12, 2002, pp. 2026-2033.
Befeler, B, et al., "Cardiovascular Dynamics During Coronary Sinus, Right Atrial, and Right Ventricular Pacing," *Am. Heart J.*, vol. 81, No. 3, Mar. 1971, pp. 372-380.
Benditt, DG et al., "Sensor-Triggered Rate-Variable Cardiac Pacing: Current Technologies and Clinical Implications," *Annals of Internal Med.*, vol. 107, No. 5, Nov. 1987, pp. 714-724.
Berkovits, B, et al., "Bifocal Demand Pacing," *Singapore Med. J.*, vol. 14, No. 3, Sep. 1973, pp. 316-319.
Berkovits, B, "Demand Pacing," *Annals of New York Academy of Sciences*, vol. 167, Art. 2, Oct. 1969, pp. 891-895.
Berkovits, B, et al.., "Future Generation Pacemakers," *Pacemaker Therapy*, L. Dreifus ed., 1983, pp. 265-276.
Blanc JJ, et al., "Recurrent Supraventricular Tachycardia: The Efficacy of a Radio Frequency System Inserted into the Coronary Sinus," *Archives des Maladies du Coeur et des Vaisseaux*, 1978, 71:687-90.
Blanc JJ, et al., "Evaluation of Different Ventricular Pacing Sites in Patients With Severe Heart Failure: Results of an Acute Hemodynamic Study," *Circulation*, vol. 96, No. 10, Nov. 1997, pp. 3273-3277.
Blanc JJ, et al., "A Method for Permanent Transvenous Left Ventricular Pacing," *PACE*, vol. 21, Nov. 1998, pp. 2021-2024.
Bognolo, DA, "Recent Advances in Permanent Pacemaker Implantation Techniques," *Modern Cardiac Pacing*, Barold SS, ed., Futura Publishing Co., 1985, pp. 199-229.
Bristow MR, et al., "Cardiac-Resynchronization Therapy With or Without an Implantable Defibrillator in Advanced Chronic Heart Failure," *N. Engl. J. Med.*, vol. 350, 2004, 2140-50.
Burkoff, D, et al., "Influence of Pacing Site on Canine Left Ventricular Contraction," *Am. J. Physiol. (Heart Circ. Physiol.)*, 1986:20:H428-H435.
Castellanos, A, et al., "Atrial Demand and AV Sequential Pacemakers," *Pacemaker Therapy*, L. Dreifus, ed., 1983, pp. 149-164.
Castellanos, A, et al., "Cardiac Pacemakers," *Cardiac Surgery 2*, vol. 3, No. 2, D. Harken, ed., 1971, pp. 32-44.
Castellanos, A, et al., "Effects of Pacemaker Impulses on Latent Arrhythmias Produced by Intramyocardial Chemical Stimulation," *Cardiologia*, vol. 51, No. 6, 1967, pp. 340-348.
Castellanos, A, et al., "An Electrical Digitalis Tolerance Test," *Am. J. of Medical Sciences*, Nov. 1967, pp. 159-168.
Castellanos, A, et al., "The Electrocardiogram and Vectorcardiogram of Ectopic Ventricular Beats," *Acta Cardiologica*, vol. 28, No. 6, 1973, pp. 562-575.
Castellanos, A, et al., "Electronic Pacemaker Models of Parasystole: With Special Reference to Artificial Intermittent Parasystole With Phase 3 and Phase 4 Protection and to Parasystolic Modulation," *PACE*, vol. 5, No. 4, Jul. 1982, pp. 537-545.
Castellanos, A, et al., "Evaluacion Clinica De Los Marcapasos Implantados," *Boletin de la Associacion Medica de Puerto Rico*, vol. 73, No. 12, Dec. 1981, pp. 644-653.
Castellanos, A, et al., "His Bundle Recordings in Atrioventricular Nodal Alternating Wenckebach Periods Ending in 5:1 Atrioventricular Block Coexisting with Paroxysmal Atrioventricular Nodal Block," *CHEST*, vol. 74, No. 3, Sep. 1978, pp. 274-279.
Castellanos, A, et al., "Implantable Demand Pacemaker," *Brit. Heart J.*, vol. 30, 1968, pp. 29-33.
Castellanos, A, et al., "Implantable Pacemakers for Cardiac Tachyarrhythmias," *Cardiac Arrythmias: Mechanisms and Management*, A. Castellanos, ed., 1980, pp. 159-173.
Castellanos, A, et al., "A New Instrument for Automatic Monitoring and Tape Recording in Infants and Children," *Boletin de la Associacion Medica de Puerto Rico*, vol. 58, No. 7, Jul. 1966, pp. 355-359.
Castellanos, A., et al., "Pacemaker-Induced Cardiac Rhythm Disturbances," *Annals of New York Academy of Sciences*, vol. 167, No. 2, Oct. 1969, pp. 903-910.
Castellanos, A, et al., "Pacemaker Vectorcardiography," *Am. Heart J.*, vol. 75, No. 1, Jan. 1968, pp. 6-18.
Castellanos, A, et al., "Pacing in Acute Myocardial Infarction: A Programmed Introduction," *CHEST*, vol. 58, No. 2, Aug. 1970, pp. 152-163.
Castellanos, A, et al., "Preliminary Studies With an Implantable Multimodal A-V Pacemaker for Reciprocating Atrioventricular Tachycardias," *PACE*, vol. 3, No. 3, May 1980, pp. 257-265.
Castellanos, A, et al., "Repetitive Firing Occurring During Synchronized Electrical Stimulation of the Heart," *J. of Thoracic Cardiovascular Surgery*, vol. 51, No. 3, Mar. 1966, pp. 334-340.
Castellanos, A, et al., "Sextapolar Catheter Electrode for Temporary Sequential Atrioventricular Pacing," *Cardiovascular Research*, vol. 8, No. 5, Sep. 1974, pp. 712-714.
Castellanos, A, et al., "Significance of Multiple Responses Produced by Electrical Depolarization of the Heart," *Acta Cardiologica*, vol. 21, No. 2, 1966, pp. 157-166.
Castellanos, A., et al., "Simultaneous Biventricular Stimulation for Ventricular Arrhythmias," *Am. J. Cardiol.*, vol. 88, Nov. 15, 2001, pp. 1217-1218.
Castellanos, A, et al., "A Study of Arrival of Excitation at Selected Ventricular Sites during Human Bundle Branch Block Using Close Bipolar Catheter Electrodes," *CHEST*, vol. 63 No. 2, Feb. 1973, pp. 208-213.
Castellanos, A, et al., "St-qR Pattern: New Sign for Diagnosis of Anterior Myocardial Infarction During Right Ventricular Pacing," *Br. Heart J.*, vol. 35, Oct. 1973, pp. 1161-1165.
Castellanos, A, et al., "The Use of the Demand Pacemaker in Auriculo-Ventricular Conduction Disturbances," *J. of Cardiovascular Surgery*, vol. 7, No. 2, Mar.-Apr. 1966, pp. 92-96.
Castellanos, A, et al., "Ventricular-triggered Pacemaker Arrhythmias," *Brit. Heart J.*, vol. 31, 1969, pp. 546-552.
Castellanos, A, et al., "The Wedensky Effect in the Human Heart," *Brit. Heart J.*, vol. 28, 1966, pp. 276-283.
Castillo, C, et al., "Bifocal Demand Pacing," *CHEST*, vol. 59, No. 4, Apr. 1971, pp. 360-364.
Cazeau S, et al., "Effects of Multisite Biventricular Pacing in Patients With Heart Failure and Intraventricular Conduction Delay," *N. Engl. J. Med.*, vol. 344, 2001, pp. 873-880.
Chamorro et al., "Ejection VAVE; EF and Phase Histogram to Evaluate a Correct Programming of AV Delay in DDD Pacemakers," European Journal of Nuclear Medicine, vol. 8, No. 5, pp. A 36 (1983).
Chamorro, JL, et. al., "Quantification of Experimental Myocardial Infarction with 99TcGlucogeptonate," *European Journal of Nuclear Medicine*, vol. 8, No. 5, 1983, Abstract P104.
D'Aiutolo, R, and Posse, R, Tratamiento de Las Arritmias Cardiacas, Buenos Aires 1968 and English-language translation of Chapter 10.
De Teresa, E., Grandes Temas de la Medicina: Marcapasos, Nueva Lente, Madrid 1987.
Dreifus, L, et al., "Effects of AV Sequential Versus Asynchronous AV Pacing on Pulmonary Hemodynamics," *PACE*, vol. 9, No. 2, Mar.-Apr. 1986, pp. 171-177.
Ellenbogen KA, et al., Clinical Cardiac Pacing and Defibrillation, 2nd Edition, Philadelphia, W.B. Saunders Co., 2000.
Elmqvist, R, et al., "An Implantable Pacemaker for the Heart," Medical Electronics: Proceedings of the Second International Conference on Medical Electronics, Smyth, CN, ed., Jun. 1959, London, UK, Iliffe & Sons; pp. 253-254.
Escher, DJW, "Historical Aspects of Cardiac Pacing," Cardiac Pacing (2$^{nd}$ Ed.), Samet, P, et al., eds., New York, Grune & Stratton, 1979, pp. 631-643.
Etienne, Y, et al., "Evaluation of Left Ventricular Based Pacing in Patients With Congestive Heart Failure and Atrial Fibrillation," *Am. J. Cardiol.*, vol. 83, 1999, pp. 1138-1140.
Fields, J, et al., "Surgical Experience With Temporary and Permanent A-V Sequential Demand Pacing," *J. of Thoracic and Cardiovascular Surgery*, vol. 66, No. 6, Dec. 1973, pp. 865-877.
Fletcher, FW, et al., "Effect of Pacemaker Location on Cardiac Function in Complete Heart Block," *Am. J. Physiol.*, 1963; 205:1232-34.
Gabrielle, O. F., "Pacing Via Coronary Sinus," *N. Engl. J. Med.*, vol. 280, No. 4, 1969, p. 219.
Greenberg, et al., "Coronary Sinus Pacing: Clinical Follow-up," *Circulation*, vol. 57, No. 1, Jan. 1978, pp. 98-103.

(56) References Cited

OTHER PUBLICATIONS

Hayes, D., "Pacemakers" in Comprehensive Cardiovascular Medicine, EJ Topol, ed., Philadelphia, Lippincott-Raven Publishers, 1998, pp. 2099-2132.
Higgins SL, et al. "Cardiac Resynchronization Therapy for the Treatment of Heart Failure in patients With Intraventricular Conduction Delay and Malignant Ventricular Tachyarrhythmias," *J. Am. Coll. Cardiol.*, Vo. 42, No. 8, 2003, pp. 1454-1459.
Holmes, DR, et al., "Pacemaker Implantation Techniques," in Electrical Therapy for Cardiac Arrhythmias, Saksena, S, et al., eds., Philadelphia, WB Saunders Co., 1990, pp. 173-190.
Kass DA, et al., "Improved Left Ventricular mechanics From Acute VDD Pacing in Patients With Dilated Cardiomyopathy and Ventricular Conduction Delay," *Circulation*, vol. 99, No. 12, Mar. 1999, pp. 1567-1573.
Kastor, J, et al., "Variations in Discharge Rate of Demand Pacemakers Not Due to Malfunction," *Am. J. of Cardiology*, vol. 25, No. 3, Mar. 1970, pp. 344-348.
Keller, J. Walter, "Atrial and Ventricular Syncrhony: The Engineering-Physiology Interface," *Annals of the New York Academy of Sciences*, vol. 167, 1969, pp. 869-885.
Kramer, D. H et al., "Permanent Pervenous Atrial Pacing from the Coronary Vein," *Circulation*, vol. 42, 1970, pp. 427-436.
Leclercq C, et al., "Acute Hemodynamic Effects of Biventricular DDD Pacing in Patients With End-Stage Heart Failure," *J. Am. Coll. Cardiol.*, vol. 32, No. 7, Dec. 1998, pp. 1825-1831.
Lemberg, L, et al., "Demand and Bifocal Demand Pacing," *Singapore Med. J.*, vol. 14, No. 3, Sep. 1973, pp. 222.
Lemberg, L, et al., "Pacemaking on Demand in AV Block," *JAMA*, vol. 191, No. 1, Jan. 1965, pp. 106-108.
Lemberg, L, et al., "Systolic and Diastolic Pacemaker Induced Repetitive Firing in the Human Heart: Analysis of 23 Cases," *J. Electrocardiology*, vol. 2 No. 4, Oct. 1969, pp. 353-362.
Lown, B, et al., "Comparison of Alternating Current with Direct Current Electroshock Across the Closed Chest," *Am. J. of Cardiology*, Aug. 1962, pp. 223-233.
Lurie KL, et al., "Development of Multifunctional Coronary Sinus Catheter," *RBM (Revue Europeenne De Technologie Biomedicale)* 1994, 16:159-61.
Mansouratii J, et al., "Left Ventricular-based Pacing in Patients With Chronic Heart Failure: Comparison of Acute Hemodynamic Benefits According to Underlying Heart Disease," *European Journal of Heart Failure*, 2 (2000):195-99.
Maytin, O, et al., "Diagramatic Representation of Pacemaker Arrhythmias," *J. Electrocardiology*, vol. 3, No. 3-4, 1970, pp. 251-257.
Medina-Ravell, V, et al., "Management of Tachyarrhythmias With Dual-Chamber Pacemakers," *PACE*, vol. 6, No. 2, Mar.-Apr. 1983, Part II, pp. 333-345.
Medina-Ravell, V, et al., "Use of Dual-Demand AV Sequential (DVI, MN) Pacemakers in the Management of Supraventricular Tachycardias," *Pacemaker Therapy*, L. Dreifus ed., 1983, pp. 227-238.
Medtronic Model 5330 A-V Sequential Demand Pulse Generator, Technical Manual, Jun. 1978.
Miyazawa, K, et al., "Effects of Varying Pacemaker Sites on Left Ventricular Performance," *Tohoku J. exp. Med.*, 1976, 120, pp. 301-308.
Miyazawa, K, et al., "Regional Contraction Patterns of the Left Ventricle during Ventricular Pacing," *Tohoku J. exp. Med.* 1977, 122; pp. 167-174.
Moss, AJ et al., "Atrial Pacing from the Coronary Vein: Ten-Year Experience in 50 Patients with Implanted Pervenous Pacemakers," *Circulation*, vol. 57, No. 1, 1978, pp. 103-106.
Nelson, GS, et al. "Left Ventricular or Biventricular Pacing Improves Cardiac Function at Diminished Energy Cost in Patients With Dilated Cardiomyopathy and Left Bundle-Branch Block," *Circulation*, vol. 102, 2000, pp. 3053-3059.
Obel, IWP, Physiological Pacing, Pitman Medical, London, 1979.
Ogawa, S, et al., "Hemodynamic Consequences of Atrioventricular and Ventriculoatrial Pacing," *PACE*, vol. 1, No. 1, Jan.-Apr. 1978, pp. 8-15.
Popovic ZB, et al., "Noninvasive Assessment of Cardiac Resynchronization Therapy for Congestive Heart Failure Using Myocardial Strain and Left Ventricular Peak Power as Parameters of Myocardial Synchrony and Function," *J Cardiovasc Electrophys.*, vol. 13, No. 12, 2002, pp. 1203-1208.
Portillo, B, et al., "Treatment of Drug Resistant A-V Reciprocating Tachycardias With Multiprogrammable Dual Demand A-V Sequential (DVI, MN) Pacemakers," *PACE*, vol. 5, No. 6, 1982, pp. 814-825.
Prauer, H, et al., "Prolonged Electrostimulation of the Heart Through the Coronary Sinus; Report of Two Cases with Position of the Electrode Confirmed by Autopsy," *Thoraxchirugie Vaskulare Chirurgie*, 1974, 22, p. 207.
Program of the VIIth World Symposium on Cardiac Pacing, Vienna, May 1-5, 1983, in *Schrittmacher: German Journal of Cardiac Pacing*, Apr. 1983, listing De Teresa et al., "An Even More Physiological Pacing Changing the Sequence of Ventricular Activation." .
Rodriguez Bailon, I, et al., "Some Data for an Unanswered Question: Choosing the Ventricular Electrode Place," *PACE*, vol. 8, No. 3, Part II, May 1985, p. A-11.
Rogel, S, et al., "Atrioventricular Time Sequence and Myocardial Efficiency," *Archives Internationales de Physiologie et de Biochimie*, 1973, 81, 833-42.
Romero, L., et al., "Non-Invasive Evaluation of Ventricular Function and Volumes During Atrioventricular Sequential and Ventricular Pacing," *PACE*, vol. 7, No. 1, Jan. 1984, pp. 10-17.
Silva et al., "Biventricular Stimulation: A More Physiologic Pacing," $4^{th}$ European Symposium on Cardiac Pacing, May 28-31, 1989, Abstract 339, pp. 148.
Silva et al., "Biventricular Stimulation: An Approach to Physiologic Cardiac Stimulation," International Congress of Cardiology, Abstracts, pp. 132 (Nov. 1988).
Silva, "Influencia de la Localizacion de la Estimulacion Electrica Ventricular Sobre la Eficiencia Cardiaca. Estudio Experimental Y Clinico," ["Influence of the Location of the Location of Ventricular Electrical Stimulation on Cardiac Efficiency"], Tesis Doctoral para la Universidad Autonoma De Madrid Facultad de Medicina (Dated 1987) (Spanish with English-Language Translation Attached).
Program of *International Congress of Cardiology*, Marrakesh, Morocco, Nov. 4, 1988, listing Silva et al, "Biventricular Stimulation: An Approach to Physiologic Cardiac Stimulation."
Silva et al., "Epicardial Biventricular Stimulation Mimicking Activation During Sinus Rhythm. Experimental Study" *European Heart Journal*, vol. 8, Supp. 2, Sep. 1987, p. 180.
Smyth, et al., "Permanent Pervenous Atrial AV Synchronous and AV Sequential Pacing," Cardiac Pacing, Thalen, H, ed., Van Gorcum: Assen, Netherlands, 1973, p. 145.
Stokes, K, et al., "The Electrode-Biointerface-Stimulation," Modern Cardiac Pacing, Barold, SS, ed., Futura Publishing, 1985, pp. 33-78.
Sutton, R, et al., "The History of Cardiac Pacing," The Foundations of Cardiac Pacing, Futura Publishing, Mt. Kisco, NY, 1991, pp. 319-324.
Wish et al., "Optimal Left Atrioventricular Sequence in Dual Chamber Pacing-Limitations of Programmed A-V Interval," *JACC*, vol. 3, No. 7, Feb. 1984, p. 507 (Abstract).
Young JB, et al; "Combined Cardiac Resynchronization and Implantable Cardioversion Defibrillation in Advanced Chronic Heart Failure: The Miracle ICD Trial," *JAMA*, vol. 238, No. 20, pp. 2685-2694.
Zaroff, L, et al., "An Implantable Demand Pacemaker," *The Annals of Thoracic Surgery*, vol. 4, No. 5, Nov. 1967, pp. 463-467.
Zoll, P, "Resuscitation of the Heart in Ventricular Standstill by External Electrical Stimulation," *N. Engl. J. Med.*, vol. 247, No. 20, 1952, pp. 768-771.
Zuckerman, W, et al., "Clinical Applications of Demand Pacing," *Annals of the New York Academy of Sciences*, vol. 167, No. 2, Oct. 30, 1969, pp. 1055-1059.
Zuckerman, W, et al., "Clinical Experiences With a New Implantable Demand Pacemaker," *Am. J. of Cardiology*, vol. 20, Aug. 1967, pp. 232-238.

(56) References Cited

OTHER PUBLICATIONS

Benchimol et al., "Cardiac Hemodynamics During Stimulation of the Right Atrium, Right Ventricle, and Left Ventricle in Normal and Abnormal Hearts," *Circulation*, vol. 33, Jun. 1966, pp. 933-944.

Benchimol et al., "Contribution of Atrial Systole to the Cardiac Function at a Fixed and at a Variable Ventricular Rate," *The American Journal of Cardiology*, vol. 16, No. 1, Jul. 1965, pp. 11-21.

Blackburn et al., "Ventricular Pacing from the Coronary Sinus of a Patient with a Fontan Circulation," *Br. Heart J.*, 1993, (70):578-579.

Bocchiardo et al., "Efficacy of Biventricular Sensing and Treatment of Ventricular Arrhythmias," *PACE*, vol. 23, 2000 Nov. 1989-1991.

Bourassa, "Hemodynamic Studies During Intermittent Left Bundle Branch Block," *American Journal of Cardiology*, Dec. 1962, 792-799.

Bove et al., "Ventricular Interdependence," *Prog. Cardiovasc. Dis.*, Mar.-Apr. 1981; 23(5):365-388.

Bracke et al., "Extraction of Pacemaker and Implantable Cardioverter Defibrillator Leads: Patient and Lead Characteristics in Relation to the Requirement of Extraction Tools," *PACE*, Jul. 2002, (25):1037-1040.

Broka et al., "Hemodynamic Effects of Atrio-Biventricular Pacing," *Ann. Thoracic Surg.*, 1995, (60):1156.

Brownlee et al., "New Functional Configurations for Adaptive Pacemakers," *28th ACEMB*, New Orleans, Sep. 20-24, 1975, p. 84.

Brownlee et al., "Advances in ventricular synchronous demand cardiac pacemakers," *Med. Instrum.*, Mar.-Apr. 1978; 12(2):94-99.

Brownlee et al., "New Interference Sensing Demand Pacemaker Functions," *IEEE Transaction on Biomedical Engineering*, May 1978, vol. BME 25, No. 3, pp. 264-269.

Castellanos et al., "Bipolar Coronary Sinus Lead for Left Atrial and Left Ventricular Recording," *American Heart Journal*, 1971, vol. 81, No. 6, 832-836.

Castellanos et al., "Measurement of Conduction Times With Catheter Electrodes During Pacing From Different Ventricular Sites," *British Heart Journal*, 1975, (37):242-248.

Castellanos et al., "Unusual QRS Complexes Produced by Pacemaker Stimuli," *American Heart Journal*, Jun. 1969, vol. 77, No. 6, 732-742.

Cazeau et al., "Four Chamber Pacing in Dilated Cardiomyopathy," *PACE*, Nov. 1994, Part II, vol. 17, 1974-1979.

Cazeau et al., "Multisite Pacing for End-Stage Heart Failure," *PACE*, Nov. 1996, (19):1748-1757.

Cazeau et al., "Echocardiographic Modeling of Cardiac Dyssynchomy Before and During Multisite Stimulation: A Prospective Study," *PACE*, Jan. 2003, Part II, (26):137-143.

Cohen et al., "Hemodynamic Responses to Rapid Pacing: A Model for Tachycardia Differentiation," *PACE*, Nov. 1988, (11):1522-1528.

Cordis Articor Manual, Implantable P-Wave Synchronized Cardiac Pacers, Model 145, 149-Rev. 3A, Oct. 1973, pp. I-1 to VIII-1.

Curtiss et al., "Electrocardiographically Discrete Right and Left Ventricular QRS Complexes: A Case Report," *J. Electrocardiol.*, Apr. 1987; 20(2):162-168.

David et al., "Atrial Alternans: Experimental Echocardiographic and Hemodynamic Demonstration During Programmed Pacing," *Am. J. of Cardiology*, Sep. 1981, vol. 48, pp. 468-472.

Dawson et al., "Regional left ventricular wall motion in pacing induced angina," *Br. Heart J.*, 1988, 59(3):309-318.

Dawson et al., "Left ventricular filling and early diastolic function at rest and during angina in patients with coronary artery disease," *Br. Heart J.* 1989, 61(3):248-257.

De Teresa et al., "An Even More Physiological Pacing: Changing the Sequence of Ventricular Activation," Cardiac Pacing: Proceedings of the VIIth World Symposium on Cardiac Pacing, Vienna, May 1-5, 1983, Steinkopff Verlag Darmstadt 1983, pp. 395-400.

De Teresa et al., "Haemodynamics of Ventricular Depolarization Sequence During Permanent Cardiac Pacing," Cardio Stimolazione, vol. 2, No. 3, p. 225 (1984).

De Teresa et al., "Haemodynamics of Ventricular Depolarization Sequence During Permanent Cardiac Pacing," Progress in Clinical Pacing, Proceedings Ed. by Santini et al., pp. 888-894, Rome (1984).

Dreifus et al., "Use of atrial and bifocal cardiac pacemakers for treating resistant dysrhythmias," *Eur. J. Cardiol.*, Dec. 1975; 3(4):257-266.

Dreifus et al., "Effect of multiple simultaneous activation sites (biventricular pacing) on ventricular depolarization and ventricular arrhythmias," *Cardiac Pacing, Proceedings of the Vth International Symposium*, Tokyo, Mar. 1976, pp. 33-39.

Duck et al., "Vorhofsynchrone Ventrikelstimulation mit verkürzter a.v. Verzögerungszeit als Therapieprinzip der hypertrophischen obstruktiven Kardiomyopathie" "[Atrial Synchronous Ventricular Stimulation With Reduced a.v. Delay Time as a Therapeutic Principle in Hypertrophic Obstructive Cardiomyopathy]," *Z. Gesamte Inn. Med.*, Sep. 15, 1984 (39):18 437-447. (German with English-Language Abstract Attached).

Erdogan et al., "Proportion of Candidates for Cardiac Resynchronization Therapy," *PACE*, Jan. 2003, Part II, 26:152-154.

Fei et al., "Effects of Multisite Ventricular Pacing on Cardiac Function in Normal Dogs and Dogs with Heart Failure," *Journal of Cardiovascular Electrophysiology*, Jul. 1999, 10(7):935-946.

Finney, Jr., "Hemodynamic Alterations in Left Ventricular Function Consequent to Ventricular Pacing," *American J. Physiology*, 1965, 208(2):275-282.

Foster et al., "Acute Hemodynamic Effects of Atrio-Biventricular Pacing in Humans," *Annals of Thoracic Surg.*, 1995, 55:294-300.

Funke, "[Optimized Sequential Pacing of Atrium and Ventricle—A New Therapeutic Concept in the Treatment of Bradycardial Dysrhythmias]," *Herz/Kreisl.*, Oct. 1978; 10(10):479-483 (German with English-Language Abstract and English Translation Attached).

Furuta et al., "[Assessment of interaction between the left and right ventricles using pressure-volume loops in various heart diseases]," J. Cardiol., Jun. 1988; 18(2):477-491. (Japanese with English Abstract and Figure Captions).

Gasparini et al., on behalf of the Italian InSync ICD Registry Investigators, "Cardiac Resynchronization and Implantable Cardioverter Defibrillator Therapy: Preliminary Results from the InSync Implantable Cardioverter Defibrillator Italian Registry," *PACE*, Jan. 2003, 26(1):2, 148-151.

Gasparini et al., "Beneficial Effects of Biventricular Pacing in Patients with a 'Narrow' QRS," *PACE*, Jan. 2003, 26(1):2, 169-174.

Gibson et al., "Effect of Changes in Ventricular Activation on Cardiac Haemodynamics in Man: Comparison of Right Ventricular, Left Ventricular, and Simultaneous Pacing of Both Ventricles," *Br. Heart J.*, May 1971; 33(3):397-400.

Gilmore et al., "Synchronicity of Ventricular Contraction: Observations Comparing Haemodynamic Effects of Atrial and Ventricular Pacing," *Br. Heart J.*, May 1963; 25:299-307.

Greatbatch, "The Making of the Pacemaker: Celebrating Lifesaving Invention," *Prometheus Books*, 2000, pp. 1-260, particularly pp. 14-19.

Gomez-Doblas et al., "Ventricular Geometry and Heart Failure," *Rev. Esp. Cardiol.*, Jan. 1999, 52(1):47-52. Review. (Spanish with English Abstract).

Grover et al., "Endocardial Pacing Site Affects Left Ventricular End-Diastolic Volume and Performance in the Intact Anesthetized Dog," *Circulation Research*, Jul. 1983, 53(1):72-85.

Haas et al., "Pacemaker-Induced Cardiovascular Failure," Am. J. Of Cardiology, vol. 33, pp. 295-299 (Feb. 1974).

Hauser et al., "Performance of Pacemaker and Implantable Cardioverter Defibrillator Pulse Generators and Leads: Results from the Multicenter Registry," *The XIIth World Congress on Cardiac Pacing & Electrophysiology*, Hong Kong, Feb. 19-22, 2003, pp. 173-179.

Hayes et al., "Cardiac Pacing: How it Started, Where We Are, Where We Are Going," *PACE*, May 2004, 27:693-704.

Hochleitner et al., "Usefulness of Physiologic Dual-chamber Pacing in Drug-Resistant Idiopathic Dilated Cardiomyopathy," *American Journal of Cardiology*, Jul. 15, 1990 (66):198-202.

Hughes et al., "Effect of Stimulation Site on Ventricular Threshold in Dogs with Heart Block," *American Heart Journal*, Jan. 1975, 89(1):68-73.

Hughes et al., "Two to Three Years of Failure-Free Testing of a Rechargeable Pacemaker in Experimental Complete Heart Block," *Circulation*, Aug. 1976, 54(2):263-266.

(56) References Cited

OTHER PUBLICATIONS

Hughes et al., "The Effects of Electrode Position on the Detection of the Transvenous Cardiac Electrogram," *PACE*, 1980, 3(6):651-655.
Hunt et al., "Long-term Electrode Catheter Pacing from Coronary Sinus," *Medical Memoranda, British Medical Journal*, Nov. 23, 1968, pp. 495-496.
Janosik et al., "The Hemodynamic Benefit of Differential Atrioventricular Delay Intervals for Sensed and Paced Atrial Events During Physiologic Pacing," *J. Am. Coll. Cardiol.*, Aug. 1989, 14(2):499-507.
Jeffrey, Excerpts from *Machines in Our Hearts*, 2001, The John Hopkins University Press, Chapter 2, pp. 36-39, 65-66, 90-100, 118-120, 170-171, and 236-237.
Jimenez-Navarro et al., Correspondence to the Editor about "Left Ventricular Assist Device," *N. Engl. J. Med.*, Mar. 28, 2002, 346(13):1023-1025; author reply 1023-1025.
Karlöf, Ingvar, "Haemodynamic Effect of Atrial Triggered Versus Fixed Rate Pacing at Rest and During Exercise in Complete Heart Block," *Acta. Med. Scand.*, 197(3):195-206, Mar. 1975.
Kawamura et al., "[83. Experimental Study of RV-LV Simultaneous Pacing as More Physiological Pacing]," Idem Job No. 0412-137, 1982, pp. 285-286. (Japanese with English Translation).
Kennergren et al., "Cardiac Lead Extraction with a Novel Locking Stylet," *Journal of Interventional Cardiac Electrophysiology*, 2000, V.4, pp. 591-593.
Kerr et al., "Transvenous Atrial Pacing Following Amputation of the Atrial Appendage at Open Heart Surgery," *PACE*, Jul.-Aug. 1985, (8):497-501.
Kerr et al., "Atrial Pacing: Efficacy and Safety," *PACE*, Jul. 1989, 12(1)1049-1054.
Klug et al., "Pacemaker Lead Extraction With the Needle's Eye Snare for Countertraction Via a Femoral Approach," *PACE*, Jul. 2002, 25(7)1023-1028.
Lattuca et al., "Bi-Ventricular Pacing to Improve Cardiac Hemodynamics," *Clinical Research*, Oct. 1990, 38 (3):882A.
Lima et al., "Incomplete Filling and Incoordinate Contraction as Mechanisms of Hypotension during Ventricular Tachycardia in Man," Circulation, vol. 68, No. 5, pp. 928-937 (1983).
Lister et al., Effect of Pacemaker Site on Cardiac Output and Ventricular Activation in Dogs with Complete Heart Block,: Am. J. of Cardiology, vol. 14, pp. 494, 496, 500 (1964).
Magder et al., "Effect of Negative Pleural Pressure on Left Ventricular Hemodynamics," *Am. J. of Cardiology*, Sep. 1, 1983, 52(5), pp. 588-593 (Abstract Only).
Mann et al., "Importance of Pacing Site in Entrainment of Ventricular Tachycardia," J. Am. College of Cardiology, vol. 5, No. 3, pp. 781-787 (1985).
Marchlinski et al., "Atrial and Ventricular Burst Pacing from a Coronary Sinus Catheter: Relation to Position of Radiofrequency Transmitter," *PACE*, May-Jun. 1985, 8(I), 399-401.
McIntosh et al., "The Hemodynamic Consequences of Arrhythmias," *Prog. Cardiovasc. Dis*., 8(4):330-363 (1966).
*Medtech Insight*, "Hot Topics in Heart Failure," Jun./Jul. 2004, cover page and pp. 190-200.
Mehta et al., "Cardiology's 10 Greatest Discoveries of the 20th Century," *Texas Heart Institute Journal*, 2002, 9(3):164-171.
Mercando et al., "Measurement of Differences in Timing and Sequence Between Two Ventricular Electrodes as a Means of Tachycardia Differentiation," *PACE*, Nov.-Dec. 1986, 9(II):1069-1078.
Mirowski et al., "A Chronically Implanted System for Automatic Defibrillation in Active Conscious Dogs," *Circulation*, Jul. 1978; 58(1):90-94.
Mirowski et al., "Clinical Experience with the Implantable Cardioverter-Defibrillator," *Annals of the New York Academy of Sciences*, 1984, 427:297-306.
Mirowski et al., "Clinical experience with the automatic implantable defibrillator," *Arch. M. Com.*, 1985, pp. 39-42.
Mirowski et al., "The Automatic Implantable Cardioverter-Defibrillator," P*PACE*, 1984 May-Jun., Part II, 7:534-540.
Mirowski et al., "Use of the automatic implantable cardioverter-defibrillator in the treatment of malignant ventricular tachyarrhythmias," *Herz*, 1984, 9(2):83-89.
Mirowski et al., "Clinical Performance of the Implantable Cardioverter-Defibrillator," *PACE*, Nov.-Dec. 1984, Part II, 7:1345-1350.
Molhoek et al., "QRS Duration and Shortening to Predict Clinical Response to Cardiac Resynchronization Therapy in Patients with End-Stage Heart Failure," *PACE*, Mar. 2004, 27:308-313.
Moore et al., "Electrophysiological Studies on Pacing Techniques to Prevent Ventricular Fibrillation," Chapter 22 from *Nonpharmacological Therapy of Tachyarrhythmias*, Futura Pub. Co., 1987, pp. 345-358.
Mortensen et al., "Sequential Biventricular Pacing: Evaluation of Safety and Efficacy," *PACE*, Mar. 2004, 27:339-345.
Moss, "Long-Term Pervenous Atrial Pacing From the Proximal Portion of the Coronary Vein," *JAMA*, Jul. 28, 1969, 209(4):543-545.
Moulopoulos et al., "Effect of Site and Intensity of Pacing on Left Ventricular Performance," J. Electocardiology, 16(4):409-415 (1983).
Mower et al., "Unusual Patterns of Conduction Produced by Pacemaker Stimuli," *Am. Heart J.*, Jul. 1967; 74(1):24-28.
Mower et al., "Automatic Implantable Cardioverter-Defibrillator Structural Characteristics," PACE, Nov.-Dec. 1984, 7(No. 6, Pt 2):1331-1337.
Navarro-Lopez et al., "Guideline 8. Criteria for Hospitalization," *Rev. Esp. Cardiol.*, 1997, 50(Supp. 1):47-48. (Spanish with English abstract).
Navarro-Lopez et al., "Guideline 1. Diagnosis of Heart Failure and Ventricular Dysfunction," *Rev. Esp. Cardiol.*, 1997, 50(Supp. 1):3-8 (Spanish with English abstract).
Navarro-Lopez et al., "Guideline 4. Management of Congestive Heart Failure," *Rev. Esp. Cardiol.*, 1997, 50(Supp. 1):27-31. (Spanish with English abstract).
Navarro-Lopez et al., "Guidelines for the Diagnosis and Management of Heart Failure and Cardiogenic Shock," *Rev. Esp. Cardiol.*, 1999, 52(Supp. 2):1-54. (Spanish with English abstract).
Ong et al., "Cephalic vein guide wire technique for implantation of permanent pacemakers," *American Heart Journal*, Oct. 1987, 4(1):753-756.
Park et al., "Effect of Alteration of Left Ventricular Activation Sequence on the Left Ventricular End-Systolic Pressure-Volume Relation in Closed-Chest Dogs," *Circulation Research*, vol. 57, No. 5, Nov. 1985, pp. 706-717.
Patel et al., Letters to the Editor: "Coronary Sinus Pacing," *Circulation*, vol. 58, No. 1, Jul. 1978, pp. 187-189.
Peschar et al., "Left Ventricular Septal and Apex Pacing for Optimal Pump Function in Canine Hearts," *Journal of the American College of Cardiology*, 2003, 41(7):1218-1226.
Platia et al., "Management of the Prolonged QT Syndrome and Recurrent Ventricular Fibrillation with an Implantable Automatic Cardioverter-Defibrillator," *Clinical Cardiology*, 1985, 8:490-493.
Platia et al. "Sensitivity of various extrastimuls techniques in patients with serious ventricular arrhythmias," *American Heart Journal*, Oct. 1983, 106(4):698-703.
Platia et al., "Treatment of Malignant Ventricular Arrhythmias With Endocardial Resection and Implantation of the Automatic Cardioverter-Defibrillator," *The New England Journal of Medicine*, Jan. 1986, 314(4):213-216.
Prinzen et al., "Relation Between the Pacing Induced Sequence of Activation and Left Ventricular Pump Function in Animals," *PACE*, Apr. 2002, Part I, 25(4):484-498.
Reid et al., "Implantable Cardioverter-Defibrillator: Patient Selection and Implantation Protocol," *PACE*, Nov.-Dec. 1984, Part II, 7:1338-1344.
Reid et al., "Clinical Evaluation of the Internal Automatic Cardioverter-Defibrillator in Survivors of Sudden Cardiac Death," *Am. J. Cardiol.*, Jun. 1983;51:1608-1609.
Ritter, "Editorial," *PACE*, Jan. 2003, Part II, 26:136.
Rogel et al., "The Universal Pacer: A synchronized-demand pacemaker," *J. Thorac. Cardiovasc. Surg.*, Mar. 1971; 61(3):466-471.

(56) References Cited

OTHER PUBLICATIONS

Rosenheck et al., "Noninstrumental Pacemaker and Defibrillator Lead Removal: The Importance of the Rotation Forces," *PACE*, vol. 25, No. 7 Jul. 2002, pp. 1029-1036.

Rosenqvist et al., "Relative Importance of Activation Sequence Compared to Atrioventricular Synchrony in Left Ventricular Function," *Am. J. of Cardiology*, vol. 67, Jan. 15, 1991, pp. 148-156.

Samet et al., "Electrical Activation and Mechanical Asynchronism in the Cardiac Cycle of the Dog," *Circulation Research*, vol. VII, Mar. 1959, pp. 228-233.

Santamore et al., "A Theoretical and Experimental Model of Ventricular Interdependence," *Basic Res. Cardiol.*, Sep.-Oct. 1986; 81(5):529-538.

Schlant et al., "Modification of the Law of the Heart: Influence of Early Contracting Areas (P)," Supp. to Circulation, vols. XXIX and XXX, Oct. 1964, pp. 153-154.

Shefer et al., "Left Ventricular Function During Physiological Cardiac Pacing: Relation to Rate, Pacing Mode, and Underlying Myocardial Disease," *PACE*, vol. 10, Mar.-Apr. 1987, pp. 315-325.

Silva, "Influencia de la Localizacion de la Estimulacion Electrica Ventricular Sobre la Eficiencia Cardiaca. Estudio Experimental Y Clinico," Tesis Doctoral para la Universidad Autonoma De Madrid Facultad de Medicine (1987), pp. 1-150 (Doctoral Thesis, in Spanish).

Sodi-Pollares et al., "General Considerations About the Activation Process of the Heart," *Deductive and Polyparametric Electrocardiography*, 1970, pp. 30-41.

Takeshita et al., "Effect of Intermittent Left Bundle Branch Block on Left Ventricular Performance," *Am. J. of Medicine*, vol. 56, Feb. 1974, pp. 251-255.

Tsagaris et al., "Species Variablility in Hemodynamic Response to Paired-Pulse Stimulation," *Am. J. of Physiology*, Jun. 1969, 216(6):1409-1417.

Tyers, "Comparison of the Effect on Cardiac Function of Single-Site and Simultaneous Multiple-Site Ventricular Stimulation After A-V Block," J. Thoracic and Cardiovas. Sur., vol. 59, No. 2, pp. 211-217 (1970).

Tyers et al., "A New Device for Nonoperative Repair of Internal Cardiac Pacemakers," *Archives of Surgery*, Jun. 1966, vol. 92:901-904.

Tyers, "Maximum Cardiac Performance After Complete Heart Block," *Surgical Forum*, vol. XVIII, American College of Surgeons, 1967, pp. 132-133.

Tyers, "Optimal electrode implantation site for asynchronous dipolar cardiac pacing," *Annals of Surgery*, Feb. 1968,167(2):168-179.

Tyers et al., "An Integrated Program for Safe Permanent Internal Cardiac Pacing," *The Journal of Cardiovascular Surgery*, 11th World Congress of International Cardiovascular Society, Barcelona, Sep. 27-29, 1973, Special issue, pp. 163-166.

Tyers et al., "Effect of Site of Synchronous Unipolar Ventricular Stimulation and Volume Loading on Cardiac Function," *J. Surg. Res.*, Oct. 1973; 15(4):271-284.

Tyers et al., "Comparative studies of 'state of the art' and presently used clinical cardiac pacemaker electrodes," *Journal of Thoracic and Cardiovascular Surgery*, St. Louis, vol. 67, No. 6, Jun. 1974, pp. 849-856.

Tyers et al., "The Advantages of Transthoracic Placement of Permanent Cardiac Pacemaker Electrodes," *Journal of Thoracic and Cardiovascular Surgery*, Jan. 1975, 69(1):8-14.

Tyers et al., "The unfulfilled promise of demand pacing," *Journal of Thoracic and Cardiovascular Surgery*, Nov. 1976, 72(5):813-814.

Tyers et al., "Improved R-wave Detection with Intramyocardial Electrodes," 30th ACEMB, Los Angeles Hilton, Los Angeles, CA, Nov. 5-9, 1977, p. 268.

Tyers et al., "R-Wave Detection for Demand Pacing-The Superiority of Intramyocardial Over Endocardial Electrodes," *J. Surg. Res.*, Apr. 1978, 24(4):316-320.

Tyers et al., "Myocardial Stimulation Impedance: the Effects of Electrode, Physiological, and Stimulus Variables," *Annals of Thoracic Surgery*, 27(1):63-69 (1979).

Tyers et al., "Multiprogrammable Pacemakers," *Canadian Journal of Surgery*, 1981, 24(3):252-256.

Tyers et al., "Current Status and Future of Programmable Pacing," Vogel, J.H.K. (Ed.). Cardiovascular Medicine, vol. 1., Raven Press: New York, N. Y., (1982), pp. 355-362.

Tyers et al., "Current Status of Sensor-Modulated Rate-Adaptive Cardiac Pacing," *Journal of the American College of Cardiology*, 1990 15(2):412-418.

Tyers et al., "Medical Device Review in Canada," *PACE*, Mar. 1995, 18(3):472-473.

Tyers et al., "Coradial Bipolar Lead Implant and Follow-Up Experience," poster presentation at the North American Society for Pacing and Electrophysiology (NASPE), 17th Annual Scientific Sessions, Seattle, WA, May 15-18, 1996, 4 pages.

Tyers et al., "Removal of Permanent Endocardial Pacing Leads (1981-1997)," *Heartweb*, vol. 4, No. 4, Feb. 1999, (Article No. 9920003), pp. 1-8.

Tyers et al., "Bipolar leads for use with permanently implantable cardiac pacing systems: A review of limitations of traditional and coaxial configurations and the development and testing of new conductor, insulation, and electrode designs," *J. Invest. Surg.*, 1997, 10(1):1-15.

Tyers et al., "Similar indications but different methods: Should there be a consensus on optimal lead extraction techniques?", *PACE*, Jul. 2002, 25(7):1019-1022.

Tyers et al., "Bifocal/Biatrial Pacing in Clinical Practice," The XIIth World Congress on Cardiac Pacing & Electrophysiology, Hong Kong, Feb. 19-22, 2003, pp. 715-717.

Tyers et al., "Coronary sinus lead extraction," The XIIth World Congress on Cardiac Pacing & Electrophysiology, Hong Kong, Feb. 19-22, 2003, pp. 741-743.

Tyers et al., "Surgical Complications of Pacemaker Implant," The XIIth World Congress on Cardiac Pacing & Electrophysiology, Hong Kong, Feb. 19-22, 2003, pp. 745-760.

Waldo et al., "Ventricular Paired Pacing to Control Rapid Ventricular Heart Rate Following Open Heart Surgery," *Circulation*, Jan. 1976, 53(1):176-181.

Walsh et al., "Differentiation of Sinus Rhythms for Supraventricular Tachydysrhythmias by Activation Sequence and Timing," *PACE* Dec. 1990;13(12 Pt 2): 1972-9 (Abstract Only).

Watkins, Jr. et al., "Surgical Techniques for Implanting the Automatic Implantable Defibrillator," *PACE*, Nov.-Dec. 1984, Part II, 7:1357-1362.

Watkins et al., "The Treatment of Malignant Ventricular Arrhythmias with Combined Endocardial Resection and Implantation of the Automatic Defibrillator: Preliminary Report," *The Annals of Thoracic Surgery*, Jan. 1984, 37(1):60-64.

Watkins et al., "Malignant Ventricular Arrhythmias, " *The Annals of Thoracic Surgery*, Jan. 1984, 37(1):65-66.

Watkins et al., "Automatic Implantable Defibrillator," *The Journal of Thoracic and Cardiovascular Surgery*, Sep. 1983, 86(3):382-387.

Watkins et al., "Automatic Defibrillation in Man: Is It Feasible?" *The American Journal of Surgery*, Jun. 1983, 145:752-755.

Waxman et al., "Ventricular Pacing from the Middle Cardiac Vein Mimicking Supraventricular Morphology" *PACE*, vol. 2, Mar.-Apr. 1979, pp. 203-207.

William-Olsson et al., "The Effect of Pacemaker Electrode Site on Cardiac Output," J. Thoracic and Cardiovas. Surg., vol. 45, No. 5, pp. 618-621 (1963).

Witte et al., "Transvenous Atrial Synchronized Pacing," *Advances in Pacemaker Technology*, Springer-Verlag Pub., 1975, pp. 99-120.

Yoshimori, "An Experimental Study on the Site for Ventricular Pacing of a Dog Heart with Special Reference to Biventricular Pacing," *Nippon Ika Daigaku Zasshi*, vol. 54, No. 3 (1987), pp. 267-276. (Japanese with English-Language Abstract and English Translation Attached).

Zile et al., "Right Ventricular Pacing Reduces the Rate of Left Ventricular Relaxation and Filling," J. Am. Coll. Cardiol., vol. 10, No. 3, pp. 702-709 (1987).

Zipes et al., "Electrophysiologic Studies on Ventricular Fibrillation," *Cardiac Electrophysiology and Arrhythmias*, Gruni and Stratton, Pub., 1985, pp. 317-320.

(56) References Cited

OTHER PUBLICATIONS

"Evaluation of bi-atrial pacing and single site right atrial pacing for the prevention of atrial fibrillation." Y. Enjoji, et al.; Third Dept. of Internal Medicine, Toho University School of Medicine; 2002.

"Bi-atrial mapping of atrial arrhythmias." R. Lemery; Division of Cardiology, Ottawa Heart Instituate; 2002.

"Permanent atrial resynchronization by synchronous bi-atrial pacing in the preventive treatment of atrial flutter associated with high degree interactrial block." C. Daubed, et al.; Hote-Dieu, Rennes; 1994.

"Effect of Varying Pacing Waveform Shapes on Propagation and Hemodynamics in the Rabbit Heart." N.V. Thakor, Ph.D., et al.; The Mirowski Symposium; 1997.

"Effectiveness of bi-atrial pacing for reducing atrial fibrillation after coronary artery bypass graft surgery." EP Gerstenfeld, et al.; Department of Medicine, University of Mass. Medical Center; 2001.

Communication, mailed Jul. 17, 2006, in European Application No. 04755341.7.

* cited by examiner

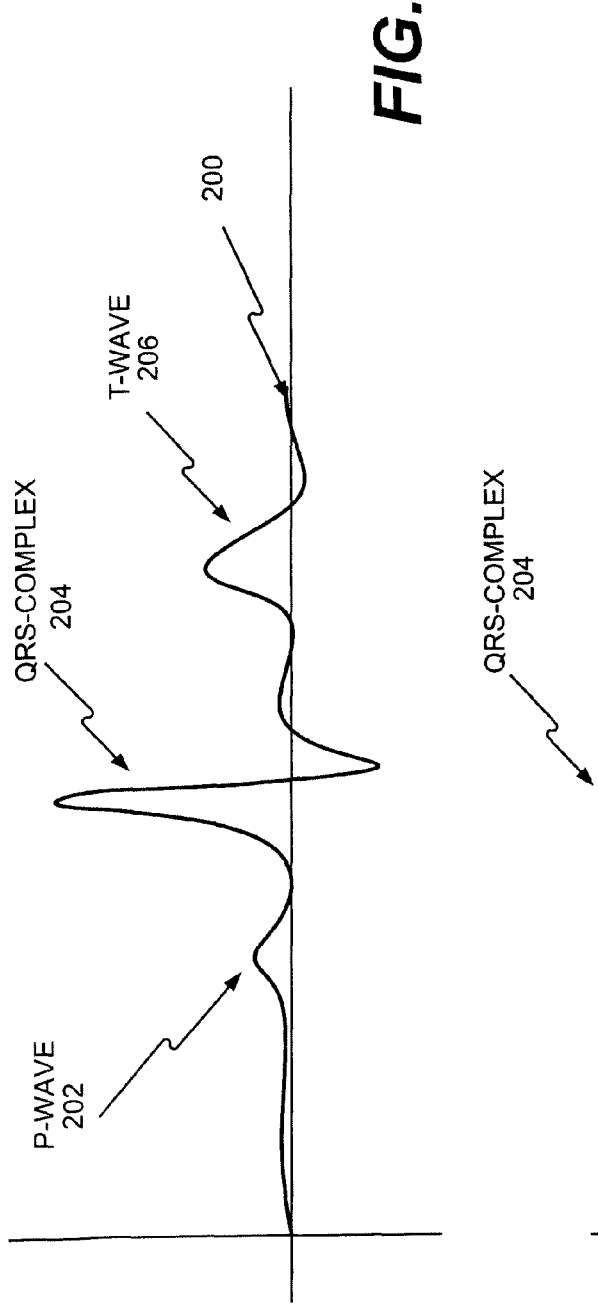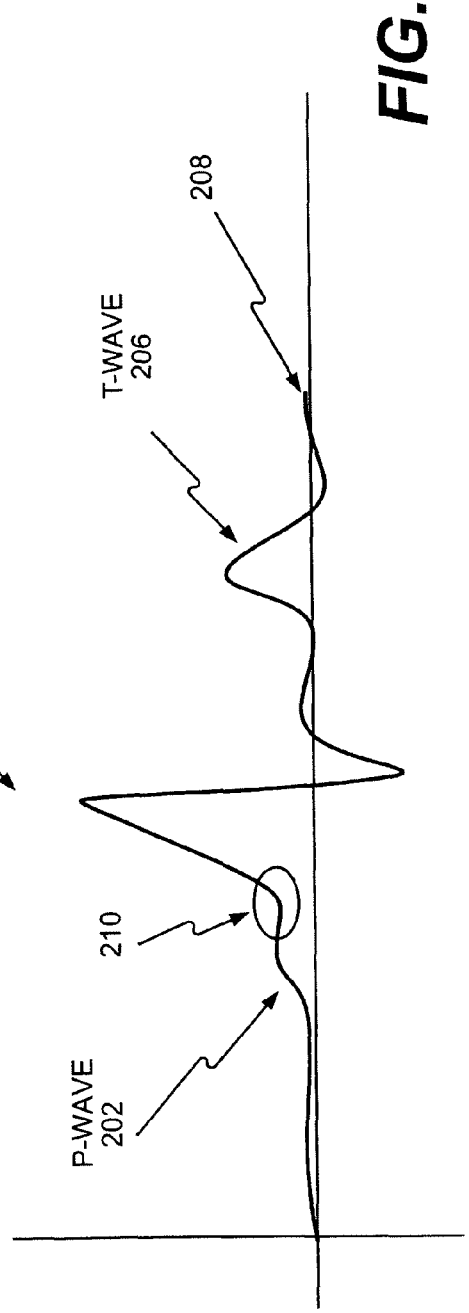

METHOD AND APPARATUS FOR PROVIDING IPSELATERAL THERAPY

CROSS-REFERENCE TO RELATED APPLICATIONS

This application is a Continuation of U.S. patent application Ser. No. 10/654,959, filed Sep. 5, 2003.

BACKGROUND OF THE INVENTION

The present invention relates to medical devices, and in particular, to methods, devices, and systems for controlling contraction of a heart. During a normal heart beat, the heart contracts in a coordinated fashion to pump blood. In particular, the heart contracts based on rhythmic electrical impulses, which are spread over the heart using specialized fibers. These rhythmic electrical pulses are initiated by the heart's natural pacemaker called the sino-atrial node (SA node). In a normal heart there is a main pathway for the electrical current, which passes from the upper part of the heart (the atria) to the lower part (the ventricles). First, the SA node initiates electrical impulses to cause the right and left atria to contract. As the atria contract, the electrical impulses from the SA node propagate to the atrial-ventricular node ("AV node"). The time these impulses take to propagate from the SA node through the AV node is known as the A-V delay. The A-V delay allows the atria to fully contract and fill the ventricles with blood. The AV node then transmits a second impulse, which causes contraction in the right and left ventricles. Blood from the ventricles then flows out of the heart and to the rest of the body. Therefore, the heart relies upon a rhythmic cycle of electrical impulses to pump blood efficiently.

A heart, however, may have cardiac defects that interfere with the rhythmic cycle or conduction of electrical impulses. For example, there are types of cardiac deficiencies that cause early stimulation and contraction in the heart. Such pre-excitation deficiencies exist, for example, where the ventricles are activated by the impulse originating from the atrium at a time earlier than would be expected if the impulse reached the ventricles by way of the normal conduction system described above. For example, the Wolff-Parkinson-White syndrome is characterized by early stimulation and contraction of the ventricles. In Wolff-Parkinson-White syndrome, there is an accessory conducting pathway that leads from the atria to the ventricles. This pathway may at times encourage a rapid rhythm. In particular, instead of allowing the next heart beat to begin at the SA node, the extra pathway can pick up an electrical impulse in the ventricles and send it back upward to the atria. When this happens, the impulse begins to travel abnormally in a rapid, circular manner, causing a rapid heart rate.

As noted above, a normal heartbeat includes an optimum A-V delay period to allow the atria to fully contract and fill the ventricles with blood. Cardiac defects, such as Wolff-Parkinson-White, cause early stimulation and contraction of the ventricles before the end of the A-V delay period, and thus, decrease the efficiency of the heart and may lead to heart failure.

Unfortunately, known stimulation devices, such as artificial pacemakers, cannot compensate for such early stimulation in the heart. While Wolff-Parkinson-White syndrome may be controlled by certain drugs or through a procedure known as catheter ablation, known implantable devices only apply stimulating pulses to assist contraction in the heart and are unable to compensate for early stimulation, such as in Wolff-Parkinson-White syndrome. Accordingly, it would be desirable to provide methods, apparatus, and systems, which can overcome these and other deficiencies in the prior art, for example, to assist the heart in contracting in a coordinated fashion.

SUMMARY

In accordance with an aspect of the present invention, methods and apparatus are provided for controlling contraction of a heart. Signals indicating electrical activity of sinus rhythm at a portion of the heart are received. An event is detected in the electrical activity at the portion of the heart. When the electrical activity at an additional portion of the heart reaches a threshold within a predetermined period of time of the event, contraction is suppressed in the additional portion of the heart based on when the electrical activity reaches the threshold.

In accordance with another aspect of the present invention, a system controls contraction of a heart. At least one sensing element is configured to receive signals indicating electrical activity of sinus rhythm from the heart. A processor is coupled to the at least one sensing element and configured to detect an event in the electrical activity. The processor provides a control signal based on when the electrical activity reaches a threshold within a predetermined period of time of the event. A signal generator is coupled to the processor and provides an electrical signal suppressing contraction in a portion of the heart responsive to the control signal.

In accordance with another aspect of the present invention, methods and apparatus are provided for controlling contraction of a heart. Signals indicating electrical activity of sinus rhythm at a portion of the heart are received. An event is detected in the electrical activity. Contraction is then suppressed in the additional portion of the heart for a predetermined period of time from the detected event.

In accordance with another aspect of the present invention, a system controls contraction of a heart. At least one sensing element is configured to receive signals indicating electrical activity of sinus rhythm from at least a portion of the heart. A processor is coupled to the at least one sensing element and configured to detect an event in the electrical activity. The processor provides a control signal in response to the detected event. A signal generator is configured to then provide an electrical signal to suppress contraction in an additional portion of the heart for a predetermined period of time from the event in response to the control signal.

In accordance with another aspect of the present invention, methods and apparatus are provided for controlling contraction of a heart. Signals that indicate electrical activity of sinus rhythm are received from the heart. Contraction of a first chamber of the heart is suppressed based on the received signals. When the electrical activity at a second chamber of the heart reaches a threshold, the suppression of contraction of the first chamber ceases.

In accordance with another aspect of the present invention, a system controls contraction of a heart. At least one sensing element is configured to receive signals indicating electrical activity of sinus rhythm of the heart. A processor is coupled to the at least one sensing element. The processor is configured to determine when a first chamber of the heart is contracting, and provides a control signal based on when the electrical activity of a second chamber of the heart reaches a threshold. A signal generator is coupled to the processor and selectively provides an electrical signal that suppresses contraction in the first chamber of the heart in response to the control signal.

Additional features and advantages of the invention will be set forth in part in the description which follows, and in part will be obvious from the description, or may be learned by practice of the invention. The features and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DESCRIPTION OF THE DRAWINGS

The accompanying drawings, which are incorporated in and constitute a part of this specification, illustrate embodiments of the invention and together with the description, serve to explain the principles of the invention.

In the figures:

FIG. 2A illustrates electrical activity of sinus rhythm associated with a normal heartbeat;

FIG. 2B illustrates electrical activity of sinus rhythm associated with a heart suffering from Wolff-Parkinson-White syndrome;

DETAILED DESCRIPTION

Methods, apparatus, and systems are provided to control contraction of the heart. At least one sensing element receives signals indicating electrical activity of sinus rhythm of the heart. The electrical activity is monitored and analyzed to detect an event. In addition, the electrical activity is monitored to detect when the electrical activity reaches a threshold within a predetermined period of time from the event. Contraction in the heart is then suppressed using, for example, one or more electrical pulses. In addition, after another predetermined period of time, the heart may then be allowed to contract naturally, or a stimulating pulse may be applied to assist the heart in contracting.

Reference will now be made in detail to exemplary embodiments of the invention, examples of which are illustrated in the accompanying drawings. Wherever possible, the same reference numbers will be used throughout the drawings to refer to the same or like parts.

Figure 1:
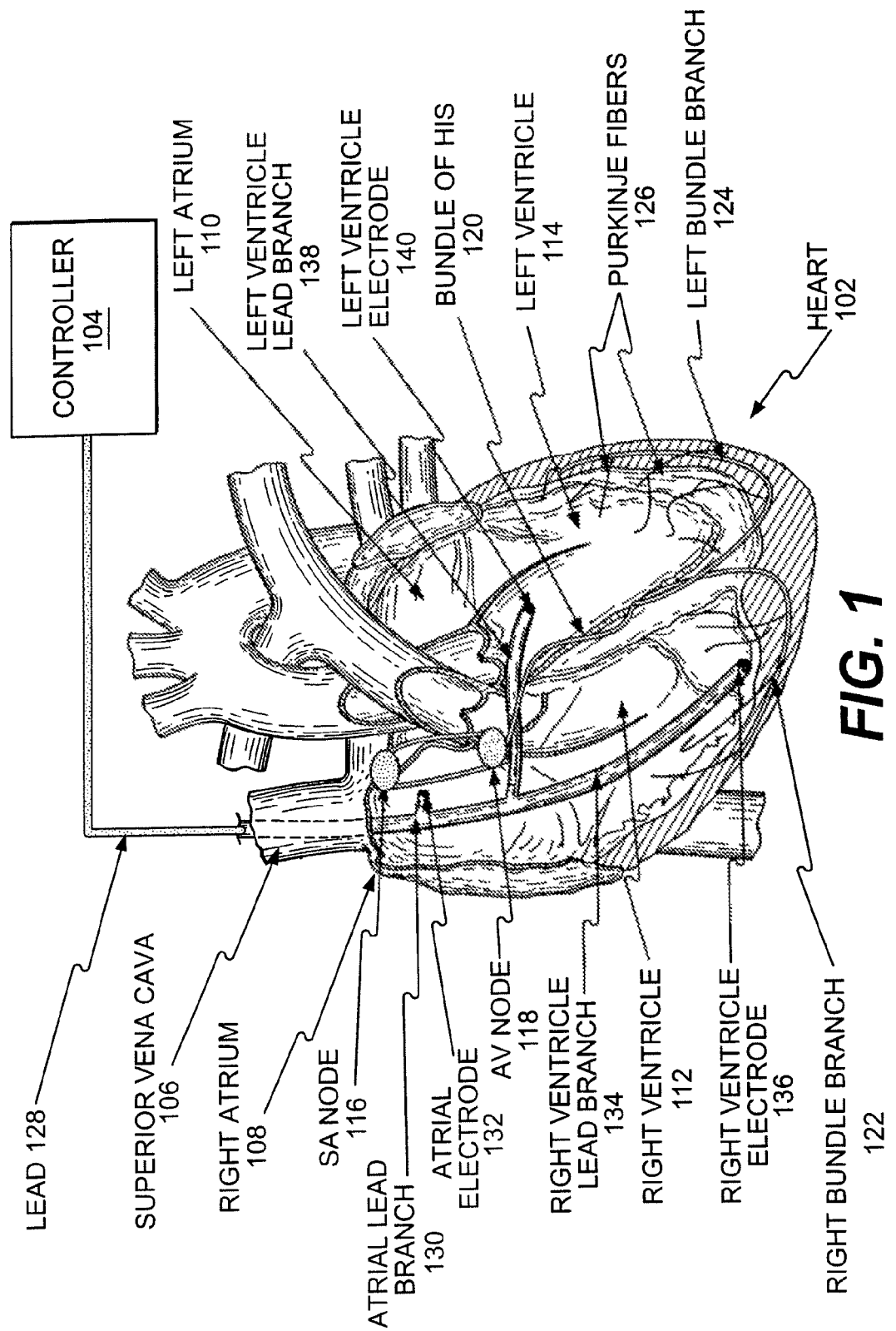
FIG. 1 illustrates an environment in which methods, apparatus, and systems may be applied consistent with the principles of the present invention.

FIG. 1 illustrates an environment in which methods, apparatus, and systems may be applied consistent with the principles of the present invention. As shown, a controller 104 may accompany a heart 102. In addition, heart 102 is shown with a superior vena cava 106, a right atrium 108, a left atrium 110, a right ventricle 112, a left ventricle 114, a sino-atrial node ("SA node") 116, an atrial-ventricular node ("AV node") 118, a Bundle of His 120, a right bundle branch 122, a left bundle branch 124, and Purkinje fibers 126.

Heart 102 normally contracts in two stages based on sinus rhythm. Sinus rhythm is where heart 102 contracts in response to electrical impulses generated from SA node 116. In order to cause contraction in the cardiac muscle of heart 102, the electrical impulses from SA node 116 must depolarize the muscle fibers above a threshold voltage of approximately −80 mV.

Accordingly, as the electrical impulses propagate from SA node 116 to AV node 118, right atrium 108 and left atrium 110 contract. Typically, the electrical impulses take approximately 120 to 200 milliseconds to travel from SA node 116 to AV node 118 (i.e., an AV delay of 120 to 200 milliseconds) and allow right ventricle 112 and left ventricle 114 to fill with blood.

Once the electrical impulses propagate to AV node 118, AV node 118 then emits an electrical impulse. This electrical impulse propagates relatively quickly over heart 102 down Bundle of His 120, and over right bundle branch 122, left bundle branch 124, and Purkinje fibers 126. In response, cardiac muscles in right ventricle 112 and left ventricle 114 depolarize and contract to pump blood to the rest of the body (not shown).

Controller 104 assists heart 102 to contract in a coordinated fashion. For example, controller 104 may apply one or more electrical pulses that suppress or stimulate contraction in the cardiac muscle of heart 102 as needed. As noted above, in order to contract, cardiac muscle in heart 102 must be depolarized above a threshold voltage of approximately −80 mV. In addition, when recovering from contraction, the cardiac muscle repolarizes to a resting voltage of approximately −90 mV. Thus, controller 104 may selectively suppress or stimulate contraction in heart 102 by applying electrical pulses to repolarize or depolarize the cardiac muscle.

Controller 104 may be coupled to heart 102 using a lead 128. Lead 128 may be installed endocardially into heart 102 via superior vena cava 106 using known surgical procedures. Lead 128 may be implemented as a hollow catheter made of an insulating material, such as silicone rubber, and provide a plurality of connection paths for carrying signals representing electrical activity of heart 102 and carrying electrical signals, such as electrical pulses, from controller 104. For example, lead 128 may further include an atrial lead branch 130, an atrial electrode 132, a right ventricle lead branch 134, a right ventricle electrode 136, a left ventricle lead branch 138, and a left ventricle electrode 140. Alternatively, controller 104 may be coupled to heart 102 using a plurality of leads. The leads may be endocardial, epicardial, or subcutaneous.

Atrial lead branch 130 provides a connection path between controller 104 and right atrium 108 for carrying signals associated with right atrium 108 and SA node 116 and electrical signals from controller 104. Although atrial lead branch 130 is shown integrated within lead 128, atrial lead branch 130 may also be implemented using a separate lead from controller 104.

Atrial electrode 132 senses electrical activity in heart 102 associated with right atrium 108 and SA node 116 and delivers electrical signals from controller 104. Atrial electrode 132 may be implemented, for example, as a helical coil of wire made of a metal, such as stainless steel. Although a single electrode is shown, a plurality of electrodes may be implemented with atrial electrode 132.

Right ventricle lead branch 132 provides a connection path for carrying signals associated with right ventricle 112 and providing electrical signals from controller 104 to right ventricle 112. Although right ventricle lead branch 134 is shown integrated within lead 128, right ventricle lead branch 134 may also be implemented using a separate lead from controller 104.

Right ventricle electrode 136 senses electrical activity in heart 102 associated with right ventricle 112, such as electrical impulses from AV node 118 and propagating over right bundle branch 122. Right ventricle electrode 136 may also be implemented, for example, as a helical coil of wire made of a metal, such as stainless steel. In addition, a plurality of electrodes may be implemented with right ventricle electrode 136.

Left ventricle lead branch 138 provides a connection path for carrying signals associated with left ventricle 114 and providing electrical signals from controller 104 to left ventricle 114. Although left ventricle lead branch 138 is shown integrated within lead 128, left ventricle lead branch 138 may also be implemented using a separate lead from controller 104.

Left ventricle electrode 140 senses electrical activity in heart 102 associated with left ventricle 114, such as electrical impulses from AV node 118 and propagating over left bundle branch 124. Left ventricle electrode 140 may also be implemented, for example, as a helical coil of wire made of a metal, such as stainless steel. In addition, a plurality of electrodes may be implemented with left ventricle electrode 140.

FIG. 2A illustrates electrical activity of sinus rhythm associated with a normal heartbeat. A waveform 200 shows one cycle of sinus rhythm and comprises a plurality of events including a P-wave 202, a QRS complex 204, and a T-wave 206. P-wave 202 indicates electrical activity that coincides with the spread of electrical impulses from SA node 116 over right atrium 108 and left atrium 110 and the contraction of these chambers. Typically, P-wave 202 has an amplitude of 0.1 mV and a duration of approximately 0.1 seconds.

QRS complex 204 indicates electrical activity that coincides with the spread of electrical impulses over right ventricle 112 and left ventricle 114 and the contraction of these chambers. Typically, QRS complex 204 occurs approximately 0.2 seconds after P-wave 202. In addition, QRS complex 204 typically has an amplitude of approximately 1 mV and a duration of approximately 0.08 seconds.

T-wave 206 indicates electrical activity that coincides with the recovery of right ventricle 112 and left ventricle 114 from contraction. Typically, T-wave 206 occurs approximately 0.2 seconds after QRS complex 204. In addition, T-wave typically has an amplitude and duration twice that of P-wave 202, i.e., approximately 0.2 mV and 0.2 seconds.

FIG. 2B illustrates electrical activity of sinus rhythm associated with a heart suffering from Wolff-Parkinson-White syndrome. Similar to waveform 200, a waveform 208 comprises P-wave 202, QRS complex 204, and T-wave 206. However, due to Wolff-Parkinson-White syndrome, waveform 208 also shows a region of premature electrical activity 210 between P-wave 202 and QRS complex 204. Premature electrical activity 210 may, for example, cause premature stimulation and contraction of right ventricle 112 and/or left ventricle 114. Although Wolff-Parkinson-White syndrome is illustrated in FIG. 2B, other types of cardiac defects, such as other types of pre-excitation defects, may be treated in accordance with the principles of the present invention.

Figure 3:
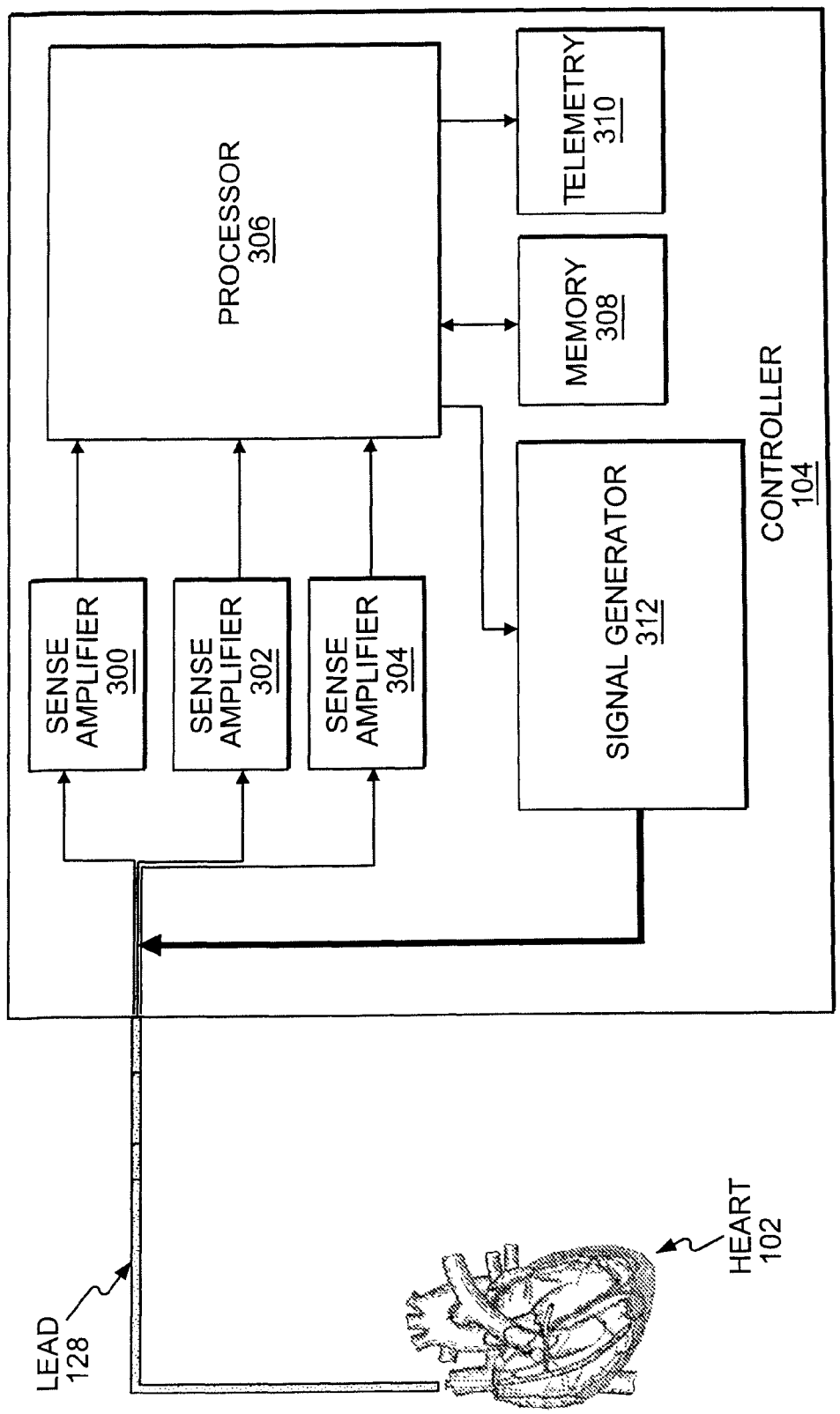
FIG. 3 illustrates a functional block diagram of a controller for controlling contraction of a heart consistent with the principles of the present invention.

FIG. 3 illustrates a functional block diagram of controller 104 for controlling contraction of heart 102 consistent with the principles of the present invention. As shown, controller 104 includes sense amplifiers 300, 302, and 304, a processor 306, a memory 308, a telemetry module 310, and a signal generator 312.

Sense amplifiers 300, 302, and 304 are coupled to atrial electrode 132, right ventricle electrode 136, and left ventricle electrode 140. Sense amplifiers 300, 302, and 304 receive signals indicating electrical activity of heart 102 from their respective electrodes, amplify these signals, and provide them to processor 306. Sense amplifiers 300, 302, and 304 may be implemented using, for example, well known circuitry.

Processor 306 receives and monitors signals from sense amplifiers 300, 302, and 304 and generates a control signal. For example, in order to treat Wolff-Parkinson-White syndrome, processor 306 may monitor the signals from sense amplifiers 300, 302, and 304 to detect when the electrical activity of heart 102 indicates premature stimulation of a ventricle, such as from premature electrical activity 210. Processor 306 may detect the possibility of premature contraction of a portion of the heart based on a variety of parameters. For example, processor 306 may monitor the electrical activity of heart 102 during sinus rhythm and detect when the electrical activity in a ventricle reaches a threshold level, such as 0.07 mV or 0.1 mV, within a predetermined period of time, such as 0.1 seconds, from P-wave 202. Processor 306 preferably detects premature contraction in a ventricle or atrium before the ventricle or atrium receives a level of stimulation after which suppression of contraction could not occur. The threshold level may be modified as required to ensure that the detection of premature stimulation occurs in time to suppress contraction. Processor 306 may use other parameters and values consistent with the principles of the present invention to detect pre-excitation of a ventricle or atrium. For example, processor 306 may detect premature stimulation based on detecting electrical activity in a portion of heart 102, detecting contraction of a portion of heart 102, detecting a rise in blood pressure, or detecting a change in impedance in a portion of heart 102. Processor 306 then provides a control signal to signal generator 312 based on the electrical activity of heart 102.

Alternatively, processor 306 may be configured to provide the control signal to signal generator 312 automatically. For example, processor 306 may be configured to provide the control signal to signal generator 312 automatically upon detecting P-wave 202.

Processor 306 may be implemented using known devices. For example, processor 306 may be implemented using a series of digital circuits. Alternatively, processor 306 may be implemented using a microprocessor, such as those manufactured by Intel Corporation.

Memory 308 provides storage for information used by processor 306. For example, memory 308 may include instructions for configuring processor 306 and instructions for monitoring the electrical activity of heart 102. Memory 308 may be implemented using known types of memory, such as a random access memory and read-only memory.

Telemetry module 310 provides diagnostic information indicating the performance of controller 104. For example, telemetry module 310 may transmit the signals received from sense amplifiers 300, 302, and 304, and signals generated by signal generator 312 via a radio link to another device, such as an external programmer (not shown). Telemetry module 310 may also collect and transmit other types of information. Telemetry module 310 may be implemented as a radio receiver/transmitter using a known radio frequency, such as 100 kHz.

Signal generator 312 generates electrical pulses for treating heart 102 via lead 128. Signal generator 312 may direct electrical pulses to one or more sites in heart 102, such as in right ventricle 112 or left ventricle 114 respectively via right ventricle lead branch 134 and left ventricle lead branch 138. In addition, as noted above, lead 128 may include a plurality of electrodes at various sites in each chamber of heart 102. Accordingly, signal generator 312 may also direct electrical pulses to one or more specific sites in each chamber of heart 102. Furthermore, signal generator 312 may be coupled to heart 102 via a plurality of leads in addition to lead 128.

Signal generator 312 may generate one or more electrical pulses to suppress contraction in heart 102 and compensate for premature stimulation, such as from premature electrical activity 210.

In addition, signal generator 312 may vary the electrical pulses delivered to heart 102 to control the suppression of contraction. Signal generator 312 may vary the number of pulses, the pulse amplitude, and pulse width. For example, signal generator 312 may generate multiple pulses to suppress contraction in heart 102 for a longer period of time than if a single pulse were used. Alternatively, signal generator 312 may increase pulse amplitude and duration to increase the period of time contraction is suppressed in heart 102.

After one or more suppression pulses from signal generator 312 are applied to the pre-excited area of heart 102 (e.g., left ventricle 114) additional suppression pulses may be applied if necessary. For example, processor 306 may determine that the right ventricle will not contract until after a standard A-V delay period causing signal generator 312 to continue to suppress contraction, for example, of left ventricle 114 until such contraction can be coordinated with contraction of right ventricle 112. For example, the present invention may allow for delay of contraction of left ventricle 114 for as much as 40 milliseconds to allow right ventricle 112 and left ventricle 114 to contract in a coordinated manner, thereby improving the hemodynamic efficiency of heart 102. In addition, if the one or more suppression pulses from signal generator 312 would cause a longer delay than desired for optimum coordinated contraction of heart 102, signal generator 312 may apply one or more stimulation pulses following the application of the one or more suppression pulses. The present invention may also be used to treat premature contraction of right ventricle 112, right atrium 108, left atrium 110, or any desired combination of chambers. For example, signal generator 312 may apply one or more pulses that suppress contraction in right ventricle 112 in order to delay the contraction of right ventricle 112 and allow right ventricle 112 to contract in a coordinated manner with left ventricle 114.

Furthermore, signal generator 312 may be configured to provide one or more electrical pulses to stimulate contraction in heart 102. For example, signal generator 312 may provide a cathodal pulse of 5 V for a duration of approximately 2 milliseconds to stimulate contraction in heart 102.

Figure 4:
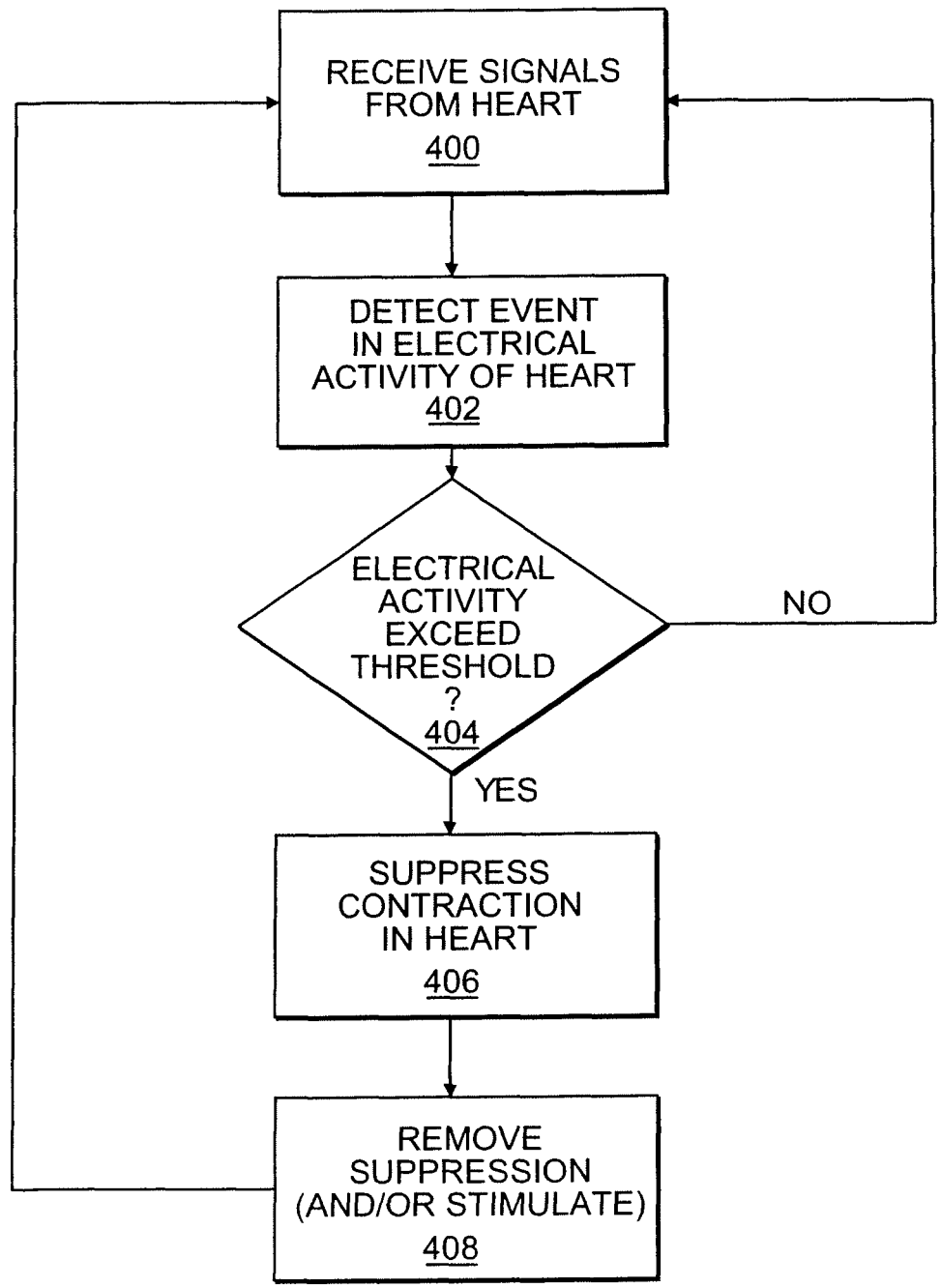
FIG. 4 illustrates a method of controlling contraction of a heart consistent with the principles of the present invention.

FIG. 4 illustrates a method of controlling contraction of a heart consistent with the principles of the present invention. In stage 400, controller 104 receives signals indicating electrical activity of heart 102. For example, atrial electrode 132, right ventricle electrode 136, and left ventricle electrode 140 may provide signals to sense amplifiers 300, 302, and 304, respectively. Sense amplifiers 300, 302, and 304 may then amplify these signals and provide them to processor 306. Processor 306 may then interpret these signals to determine the electrical activity of sinus rhythm for heart 102. In addition, processor 306 may store data from these signals in memory 306, for example, for transmission by telemetry module 310 to another device.

In stage 402, processor 306 detects an event in the electrical activity. For example, processor 306 may monitor the electrical activity for P-wave 202. In addition, processor 306 may store information related to this event, such as time and amplitude of the event, in memory 308.

In stage 404, processor 306 then detects whether the electrical activity exceeds a threshold, such as 0.07 or 0.1 mV, within a predetermined period of time, such as 0.1 seconds, from the event. If the electrical activity does not exceed the threshold within the predetermined period of time, processor 306 interprets this circumstance as a normal sinus rhythm and processing repeats at stage 400. However, if processor 306 detects that the electrical activity reaches the threshold within the predetermined period of time, then processor 306 may interpret this circumstance as premature stimulation in an area of heart 102, such as premature electrical activity 210 in left ventricle 114 and/or right ventricle 112.

In stage 406, processor 306 provides a control signal to signal generator 312 to suppress contraction in heart 102. The control signal may specify specific sites in heart 102 and the type of electrical pulses used to suppress contraction. For example, processor 306 may provide a control signal specifying either right ventricle 112, or left ventricle 114, or both.

In stage 406, in response to the control signal from processor 306, signal generator 312 applies one or more electrical pulses to heart 102 via lead 128. For example, signal generator 312 may send electrical pulses via lead 128 to right ventricle electrode 136 and/or left ventricle electrode 140.

In stage 408, signal generator 312 completes the application of the electrical pulses suppressing contraction. Processor 306 may then monitor the electrical activity of heart 102 to determine its response and whether the electrical pulses were sufficient to compensate for the premature stimulation, for example, by premature electrical activity 210. If needed, based on the response of heart 102, processor 306 may direct signal generator 312 to apply additional electrical pulses to suppress contraction for an additional period of time. Upon completion of the suppressing electrical pulses, processor 306 may allow heart 102 to contract naturally. Alternatively, processor 306 may provide a control signal to signal generator 312 to subsequently stimulate one or more sites to assist contraction in heart 102. Processing then repeats again at stage 400.

Figure 5:
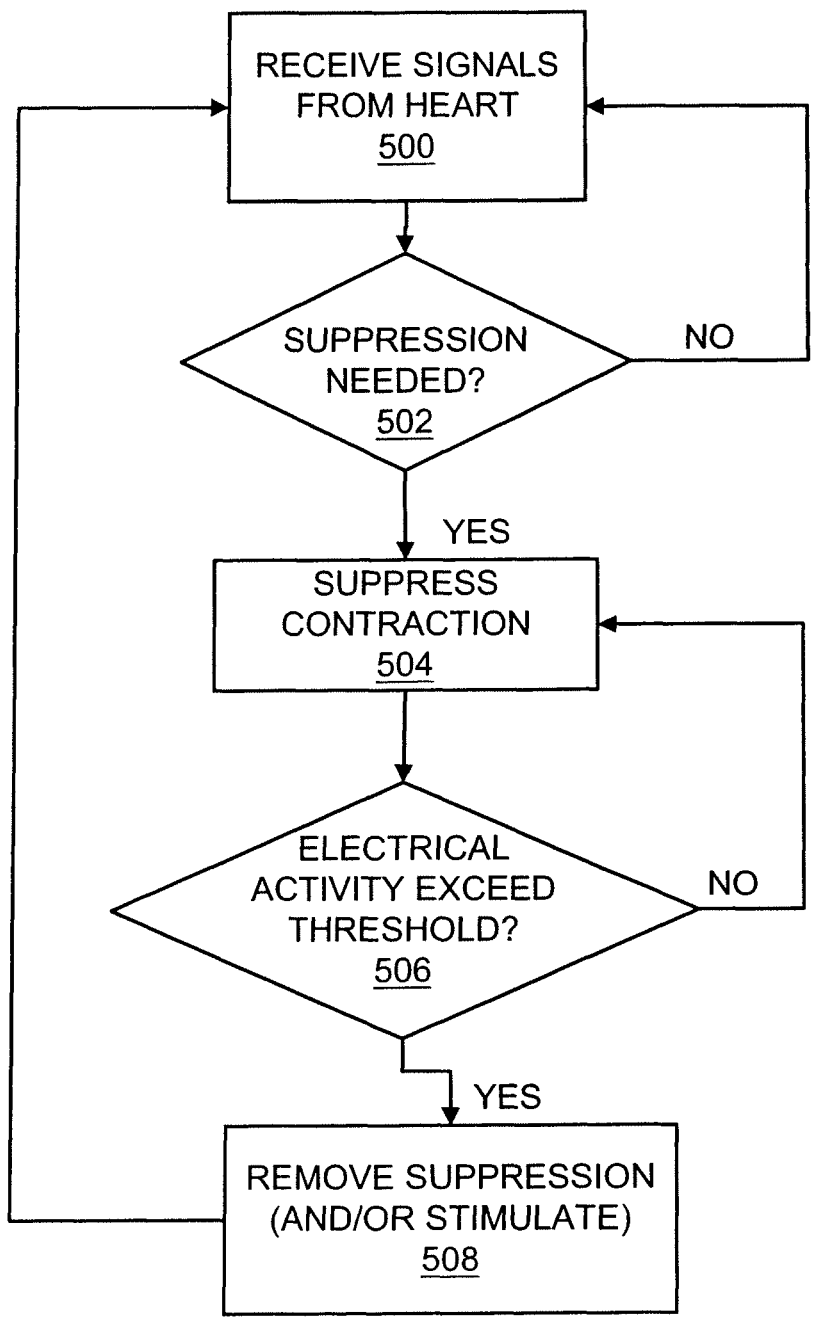
FIG. 5 illustrates another method of controlling contraction of a heart consistent with the principles of the present invention.

FIG. 5 illustrates another method of controlling contraction of a heart consistent with the principles of the present invention. In stage 500, controller 104 receives signals indicating electrical activity of heart 102. For example, atrial electrode 132, right ventricle electrode 136, and left ventricle electrode 140 may provide signals to sense amplifiers 300, 302, and 304, respectively. Sense amplifiers 300, 302, and 304 may then amplify these signals and provide them to processor 306. Processor 306 may then interpret these signals to determine the electrical activity of sinus rhythm for heart 102. In addition, processor 306 may store data from these signals in memory 306, for example, for transmission by telemetry module 310 to another device.

In stage 502, processor 306 determines whether suppression is required in one or more portions of heart 102 based on the received signals. For example, processor 306 may monitor the electrical activity of right ventricle 112 and left ventricle 114 and determine whether either ventricle will prematurely contract. Processor 306 may store information related to this premature contraction, such as the time and amplitude, in memory 308.

Processor 306 may determine whether a chamber of heart 102, such as right ventricle 112 or left ventricle 114, will prematurely contract based on whether the electrical activity in that chamber exceeds a threshold, such as 0.07 or 0.1 mV, within a predetermined period of time of contraction of another chamber of the heart, such as the right atrium. If the electrical activity does not exceed the threshold within the predetermined period of time, processor 306 may interpret this circumstance as a normal sinus rhythm and processing repeats again at stage 500. However, if processor 306 detects that the electrical activity reaches the threshold within the predetermined period of time, processor 306 may interpret this circumstance as premature stimulation in portion of heart 102, such as premature electrical activity 210 in left ventricle 114 and/or right ventricle 112. Processing may then flow to stage 504.

Alternatively, processor 306 may determine whether a first chamber of heart 102, such as right ventricle 112, will prematurely contract based on whether the electrical activity in that chamber exceeds a threshold, such as 0.07 or 0.1 mV, prior to electrical activity in a second chamber, such as left ventricle 114, exceeding a threshold, such as 0.07 or 0.1 mV. If the respective electrical activity in the first and second chambers indicates coordinated contraction, processor 306 may interpret this circumstance as a normal sinus rhythm and processing repeats again at stage 500. However, if processor 306 detects that the timing of the electrical activity in the first chamber will cause uncoordinated contraction relative to the second chamber, processor 306 may interpret this circumstance as premature stimulation in the first chamber. Processing may then flow to stage 504.

In stage 504, controller 104 suppresses contraction in the one or more portions of heart 102. In one embodiment, processor 306 provides a control signal to signal generator 312 to suppress contraction in heart 102. The control signal may specify specific sites in heart 102 and the type of electrical pulses used to suppress contraction. For example, processor 306 may provide a control signal specifying either right ventricle 112, or left ventricle 114, or both.

In response to the control signal from processor 306, signal generator 312 applies one or more electrical pulses to heart 102 via lead 128. For example, signal generator 312 may send electrical pulses via lead 128 to right ventricle electrode 136 and/or left ventricle electrode 140.

In stage 506, controller 104 determines whether to continue to suppress contraction in one or more portions of heart 102 based on the electrical activity of heart 102. For example, processor 306 may monitor the electrical activity of heart 102 to determine how heart 102 is responding to the suppression of contraction and determine when to cease suppressing contraction in heart 102.

In one embodiment, processor 306 monitors the electrical activity of heart 102 to determine when the electrical activity of a non-suppressed portion of heart 102 reaches a threshold. For example, if controller 104 is suppressing premature contraction in left ventricle 114, then processor may detect when electrical activity in right ventricle 114 reaches a threshold. If the electrical activity of heart 102 has not reached the threshold, then this indicates that one or more portions of heart 102, such as left ventricle 114, still require suppression of contraction and processing repeats again at stage 504. If the electrical activity, for example, in right ventricle 114 reaches the threshold, then processing flows to stage 508.

In stage 508, controller 104 ceases the suppression of contraction in the one or more portions of heart 102. In one embodiment, signal generator 312 ceases applying electrical pulses to suppress contraction in response to a control signal from processor 306. The control signal from processor 306 may be generated when the electrical activity in heart 102 exceeds a threshold. In addition, processor 306 may be configured to cease suppressing contraction after a delay period.

Furthermore, upon ceasing suppression, processor 306 may allow heart 102 to contract naturally, or provide a control signal to signal generator 312 to subsequently stimulate one or more sites to assist contraction in heart 102. Processing then repeats again at stage 500.

A method and apparatus for providing ipselateral therapy has been described. It will be apparent to those skilled in the art that other variations of the present invention are possible without departing from the scope of the invention as disclosed. Further, any reference to claim elements in the singular, for example, using the articles "a," "an," or "the" is not to be construed as limiting the element to the singular.

What is claimed is:

1. A method of causing a controller to control contraction of a heart, comprising:
   receiving signals, at the controller, indicating electrical activity corresponding to a contraction phase of a sinus rhythm cycle at an atrium of the heart;
   detecting, with the controller, depolarization of the atrium based on the received signals;
   detecting, with the controller, electrical activity at a second portion of the heart within a predetermined period of time relative to detection of the depolarization of the atrium of the heart, the predetermined period of time being shorter than a duration of the sinus rhythm cycle;
   applying to the second portion of the heart an electrical stimulation via the controller to repolarize the second portion of the heart to a voltage less than a contraction threshold when a magnitude of the electrical activity detected at the second portion of the heart exceeds a predetermined threshold within the predetermined period of time relative to the detection of the depolarization of the atrium of the heart, the electrical stimulation being applied prior to premature depolarization of the second portion of the heart in response to the electrical activity at the atrium of the heart;
   ceasing application of the electrical stimulation to the second portion of the heart to allow depolarization and contraction thereof during the contraction phase of the sinus rhythm cycle.

2. The method of claim 1, wherein the electrical stimulation to repolarize the second portion of the heart is applied to a ventricle.

3. The method of claim 1, wherein the signals indicating electrical activity of the atrium of the heart include depolarization signals from both the left atrium and the right atrium.

4. The method of claim 1, wherein detecting depolarization of the atrium in the electrical activity comprises detecting a P-wave in an electrocardiogram signal of the heart.

5. The method of claim 1, further comprising:
   applying a pulse to stimulate contraction in the second portion of the heart after the electrical stimulation to repolarize the second portion of the heart.

6. The method of claim 5, wherein applying the pulse to stimulate contraction comprises applying the pulse to stimulate contraction in a ventricle.

7. An apparatus for controlling contraction of a heart, comprising:
   means for receiving signals indicating electrical activity corresponding to a contraction phase of a sinus rhythm cycle at an atrium of the heart;
   means for detecting depolarization of the atrium based on the received signals;
   means for detecting when electrical activity at a second portion of the heart reaches a predetermined threshold within a predetermined period of time relative to depolarization of the atrium, the predetermined period of time being shorter than a duration of the sinus rhythm cycle;
   means for suppressing contraction in the second portion of the heart when the electrical activity of the second portion of the heart exceeds the predetermined threshold within the predetermined period of time relative to depolarization of the atrium, the contraction in the second portion of the heart being suppressed prior to premature depolarization of the second portion of the heart in response to depolarization of the atrium of the heart; and means for ceasing suppression of the contraction in the second portion of the heart to allow the second portion of the heart to depolarize and contract during the contraction phase of the sinus rhythm cycle.

8. An apparatus to control contraction of a heart, comprising:

at least one sense amplifier to receive signals indicating electrical activity corresponding to a contraction phase of a sinus rhythm cycle at an atrium of the heart;

a processor to detect depolarization of the atrium based on the received signals, the processor detecting electrical activity in a second portion of the heart within a predetermined time period relative to depolarization of the atrium of the heart, the predetermined time period being shorter than a duration of the sinus rhythm cycle; and a generator configured to apply electrical stimulation to the second portion of the heart to repolarize the second portion of the heart below a contraction threshold when the electrical activity of the second portion of the heart exceeds a predetermined threshold within the predetermined time period relative to the depolarization of the atrium of the heart, the generator applying the electrical stimulation prior to premature depolarization of the second portion of the heart in response to the depolarization of the atrium of the heart, wherein the processor causes the generator to cease application of the electrical stimulation to allow the second portion of the heart to depolarize and contract within the contraction phase of the sinus rhythm cycle.

9. The apparatus according to claim 8, wherein the processor detects electrical activity in the second portion of the heart by monitoring blood pressure or an electrical impedance of the second portion of the heart.

10. The method according to claim 1, wherein the electrical stimulation is applied to the second portion of the heart between a P-wave and a QRS complex of the sinus rhythm cycle.

\* \* \* \* \*